US012605135B2

(12) United States Patent
Seto

(10) Patent No.: US 12,605,135 B2
(45) Date of Patent: Apr. 21, 2026

(54) MEDICAL DEVICE, SCANNING METHOD, AND STORAGE MEDIUM

(71) Applicant: GE Precision Healthcare LLC, Wauwatosa, WI (US)

(72) Inventor: Masaru Seto, Hino (JP)

(73) Assignee: GE Precision Healthcare LLC, Wauwatosa, WI (US)

( * ) Notice: Subject to any disclaimer, the term of this patent is extended or adjusted under 35 U.S.C. 154(b) by 383 days.

(21) Appl. No.: 18/324,471

(22) Filed: May 26, 2023

(65) Prior Publication Data

US 2023/0380790 A1 Nov. 30, 2023

(30) Foreign Application Priority Data

May 30, 2022 (JP) ................................. 2022-088114

(51) Int. Cl.
*A61B 6/00* (2024.01)
*A61B 6/03* (2006.01)
*A61B 6/46* (2024.01)

(52) U.S. Cl.
CPC .............. *A61B 6/542* (2013.01); *A61B 6/032* (2013.01); *A61B 6/463* (2013.01)

(58) Field of Classification Search
CPC ......... A61B 6/542; A61B 6/032; A61B 6/463; A61B 6/501; A61B 6/488; A61B 6/035; A61B 6/0421; A61B 6/4429; G16H 40/63
See application file for complete search history.

(56) References Cited

U.S. PATENT DOCUMENTS

2010/0232566 A1* 9/2010 Hirokawa .............. A61B 6/032
378/5

FOREIGN PATENT DOCUMENTS

| | | |
|---|---|---|
| JP | 2010269048 A | 12/2010 |
| JP | 2021020054 A | 2/2021 |
| WO | 2009020136 A1 | 2/2009 |

OTHER PUBLICATIONS

JP patent application 2022-088114 filed May 30, 2022—Office Action issued Jun. 7, 2023; Machine Translation; 4 pages.
JP2010-269048 English Abstract; Espacenet search results Sep. 12, 2023; 1 page.
JP2021-020054 English Abstract; Espacenet search results Sep. 12, 2023; 1 page.

* cited by examiner

*Primary Examiner* — Courtney D Thomas

(57) ABSTRACT

A medical device is described. The medical device includes a gantry including an X-ray tube that can rotate on a path centered on a rotation axis and an X-ray controller that controls the X-ray tube, a table on which a subject can lie, and at least one processor. The medical device executes a first scan on the subject, where the processor executes operations including determining a first position on the path for arranging the X-ray tube for the first scan based on the direction the portion of the subject body to be imaged is facing, and controlling the X-ray tube by means of the X-ray controller such that the X-ray tube irradiates X-rays from said first position.

18 Claims, 32 Drawing Sheets

16

17

18

161

171

181

26

27

28

181

MEDICAL DEVICE, SCANNING METHOD, AND STORAGE MEDIUM

REFERENCE TO RELATED APPLICATIONS

This application claims priority to Japanese Application No. 2022-088114, filed on May 30, 2022, the disclosure of which is incorporated herein by reference in its entirety.

TECHNICAL FIELD

The present invention relates to a medical device including an X-ray tube, a scanning method for executing a scan of a subject body using the medical device, and a storage medium on which instructions for controlling the medical device are recorded.

BACKGROUND ART

A Computed Tomography (CT) device is known as a medical device that noninvasively images a subject body. CT devices can capture images of a portion to be imaged in a short period of time, and therefore have become widespread in hospitals and other medical facilities.

SUMMARY OF THE INVENTION

When performing an examination of a subject body, an operator lays the subject body on a table so that the subject body lies on the table in a posture (body position) suitable for the examination. For example, when imaging the head of the subject body, the operator generally lays the subject body on a table in a supine position.

In the supine position, the subject body desirably lies on a table with their face facing directly upward. However, if facing the face of the subject body directly upward is not possible because the subject body is elderly or suffering from illness, the face of the subject body may face, for example, obliquely upward.

In this case, securing the head of the subject body using a head folder or the like so that the face of the subject body faces directly upward can be considered. However, for a subject body where there is difficulty in directing his/her face directly upward, forcibly causing the face to face directly upward using the head folder may impose a heavy burden on the body of the subject body. Therefore, in general, scanning is performed in a state where the face of the subject body faces obliquely upward. For example, when a scout scan is executed, a scout image is acquired in a state where the face of the subject body faces obliquely upward.

The scout image is used for setting the scan range of the subject body, and the operator sets the scan range of the subject body with reference to the scout image. In addition, in recent years, a technique of executing segmentation of a scout image and automatically setting a scan range of a subject body based on the result of the segmentation, and a technique of specifying an organ having high sensitivity to radiation based on a result of the segmentation of a scout image and selectively reducing exposure to the specified organ have also been researched and developed.

However, since imaging in the supine position is based on the assumption that the face of the subject body faces directly upward, if a scout image is acquired in a state where the face of the subject body faces obliquely upward, there is a problem in that the accuracy of segmentation decreases, and the automatically set scan range deviates from a desired range or the specified region of the organ deviates from the region where the organ actually exists.

In the example described above, a problem was described for the case of imaging a head of a subject body, but the same problem exists for imaging portions of the subject body other than the head.

Here, providing technology enabling acquiring substantially the same image as the image acquired when the portion to be imaged is facing the desired direction even if the subject body is scanned while the portion to be imaged cannot face the desired direction is desirable.

A first aspect of the present invention is a medical device, including a gantry including an X-ray tube that can rotate on a path centered on a rotation axis and an X-ray controller that controls the X-ray tube, a table on which a subject body can lie, and at least one processor, the medical device executing a first scan on the subject body, wherein the processor executes operations including determining a first position on the path for arranging the X-ray tube for the first scan based on the direction the portion of the subject body to be imaged is facing, and controlling the X-ray tube by means of the X-ray controller such that the X-ray tube irradiates X-rays from said first position.

In addition, a second aspect of the present invention is a method of scanning, comprising executing a first scan on a subject body using a medical device including: a gantry having an X-ray tube that can rotate on a path centered on a rotation axis and an X-ray controller that controls the X-ray tube, and a table on which the subject body can lie, determining a first position on the path for positioning the X-ray tube for the first scan based on the direction that the portion of the subject body to be imaged is facing, and controlling the X-ray tube by means of the X-ray controller such that the X-ray tube irradiates X-rays from said first position.

In addition, a third aspect of the present invention is a storage medium readable by a computer in a non-transitory manner storing one or more instructions executable by one or more processors, wherein the storage medium is contained in the medical device that includes a gantry having an X-ray tube that can rotate on a path centered on a rotation axis and an X-ray controller that controls the X-ray tube and a table on which a subject body can lie, and the one or more instructions determines, upon execution by the one or more processors, the first position on the path for positioning the X-ray tube for the first scan based on the direction the portion of the subject body faces and controls the X-ray tube by means of the X-ray controller such that the X-ray tube irradiates X-rays from said first position.

In the present invention, the direction of the portion to be imaged is obtained, and the position of the X-ray tube is determined based on the direction of the portion to be imaged. Thereby enabling acquiring substantially the same image as the image acquired when the portion to be imaged is facing the desired direction even if the subject body is scanned while the portion to be imaged cannot face the desired direction.

DESCRIPTION OF EMBODIMENTS

Figure 1:
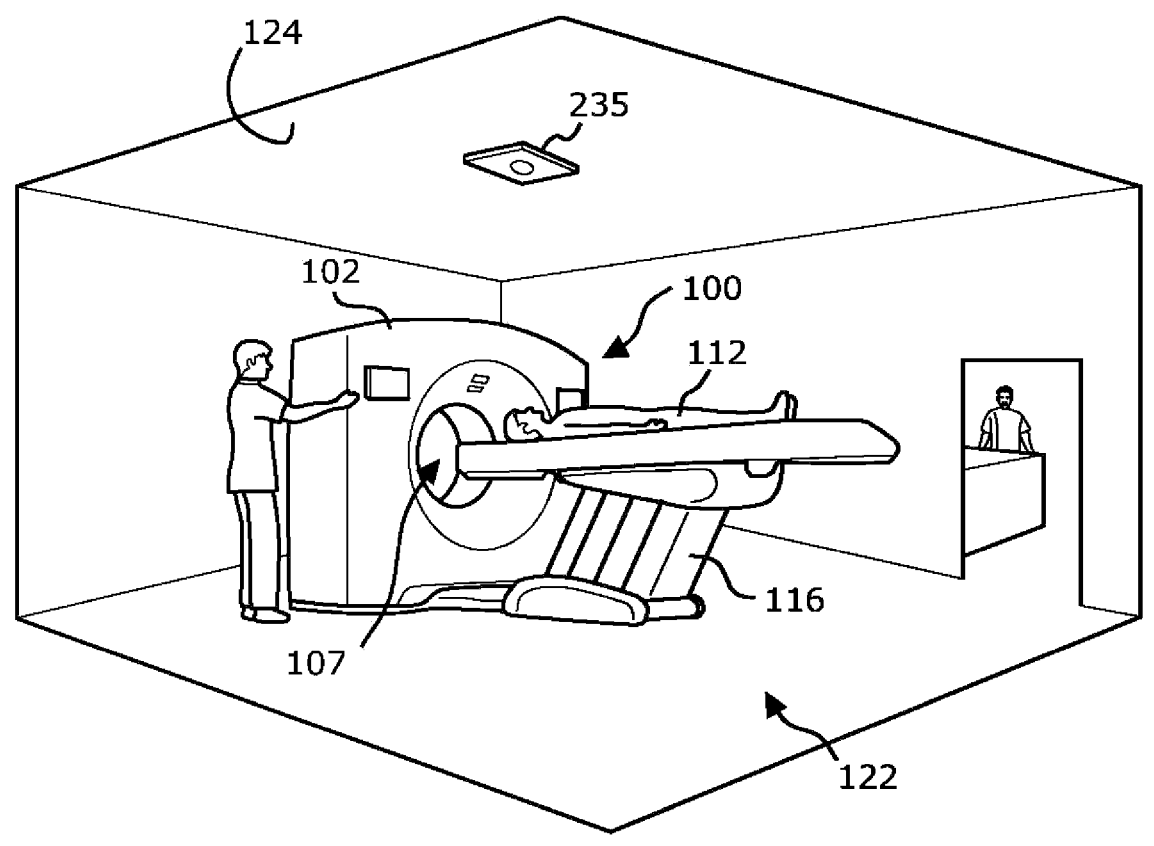
FIG. 1 is a perspective view of the CT device 100 of Embodiment 1.
Figure 2:
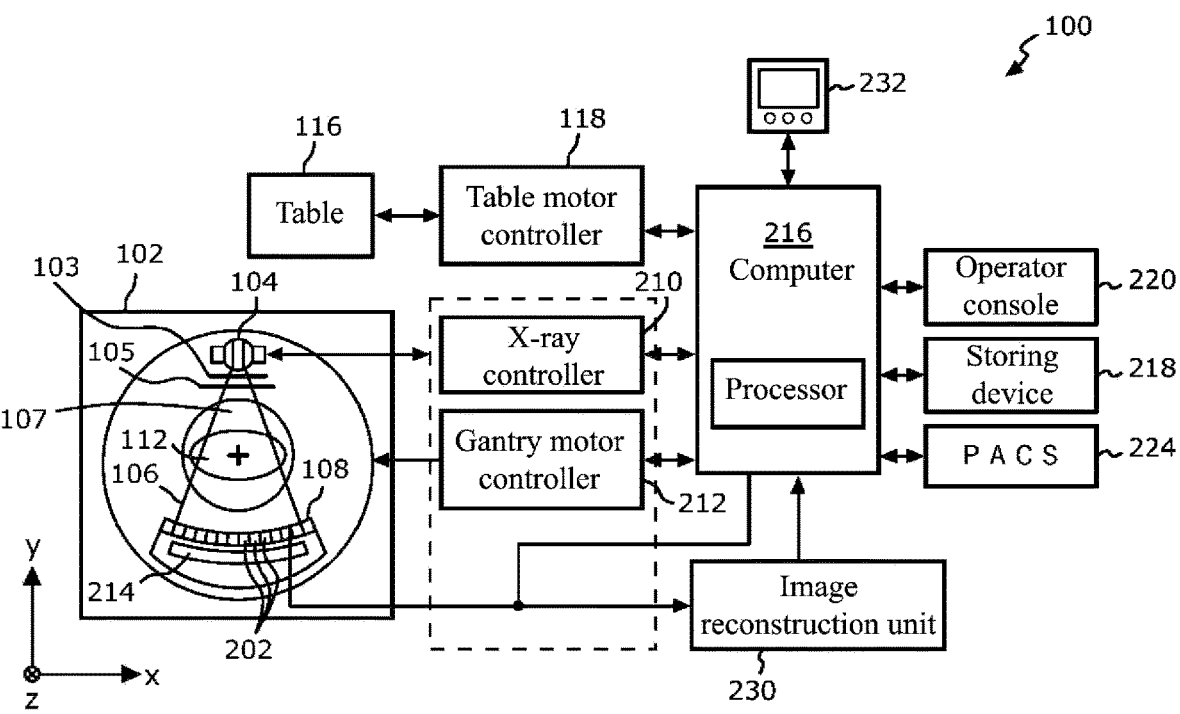
FIG. 2 is a block diagram of the CT device 100.

An embodiment for carrying out the invention will be described below, but the present invention is not limited to the following embodiment. FIG. 1 is a perspective view of a CT device 100 of Embodiment 1. FIG. 2 is a block diagram of the CT device 100.

The CT device 100 includes a gantry 102 and a table 116. The gantry 102 and the table 116 are installed in a scan room 122. The gantry 102 has an opening 107 through which a subject body 112 is transported to scan the subject body 112. The gantry 102 is equipped with an X-ray tube 104, a filter part 103, a front collimator 105, and an X-ray detector 108.

The X-ray tube 104 generates X-rays when a prescribed voltage is applied to the cathode-anode tube. The X-ray tube 104 is configured to be rotatable on a path centered on the rotation axis within the XY plane. Here, the Z direction represents the body axis direction, the Y direction represents the vertical direction (the height direction of the table 116), and the X direction represents the direction perpendicular to the Z and Y directions. An X-ray tube compatible with a rapid kV switching system capable of switching the tube voltage may be provided as the X-ray tube 104. Moreover, although the CT device 100 includes one X-ray tube 104 in Embodiment 1, two X-ray tubes may be included.

The filter part 103 includes, for example, a flat plate filter and/or a bow-tie filter. The front collimator 105 is a component that narrows the X-ray irradiation range so that X-rays are not emitted in unwanted areas. The X-ray detector 108 includes a plurality of detector elements 202. A plurality of detector elements 202 detect an X-ray beam 106 that is irradiated from the X-ray tube 104 and passes through the subject body 112, such as a patient. Thus, the X-ray detector 108 can acquire projection data for each view.

The projection data detected by the X-ray detector 108 is collected by a Data Acquisition System (DAS) 214. The DAS 214 performs prescribed processing, including sampling and digital conversion, on the collected projection data. The processed projection data is transmitted to a computer 216. Data from the DAS 214 may be stored in a storing device 218 by the computer 216. The storing device 218 includes one or more storage media that store programs as well as instructions to be executed by the processor. The storage medium can be, for example, one or more non-transitory, computer-readable storage media. The storing device 218 may include, for example, hard disk drives, floppy disk drives, compact disc read/write (CD-R/W) drives, digital versatile disk (DVD) drives, flash drives, and/or solid state storage drives. The computer 216 includes one or a plurality of processors. The computer 216 uses one or a plurality of processors to output commands and parameters to the DAS 214, X-ray controller 210, and/or gantry motor controller 212, to control system operations such as data acquisition and/or processing. In addition, the computer 216 uses one or more processors to execute signal processing, data processing, image processing, and the like in each step of the flow described below (see FIG. 14, FIG. 23, FIG. 26, and FIG. 29).

An operator console 220 is linked to the computer 216. An operator can enter prescribed operator inputs related to the operation of the CT device 100 into the computer 216 by operating the operator console 220. The computer 216 receives operator input, including commands and/or scan parameters, via the operator console 220 and controls system operation based on that operator input. The operator console 220 can include a keyboard (not shown) or touch screen for the operator to specify commands and/or scan parameters.

The X-ray controller 210 controls the X-ray tube 104 based on control signals from the computer 216. In addition, a gantry motor controller 212 also controls the gantry motors to rotate structural elements such as the X-ray tube 104 and the X-ray detector 108 based on control signals from the computer 216.

FIG. 2 illustrates only one operator console 220, but two or more operator consoles may be linked to the computer 216. In addition, the CT device 100 may also allow a plurality of remotely located displays, printers, workstations, and/or similar devices to be linked via, for example, a wired and/or wireless network.

In an embodiment, for example, the CT device 100 may include or be linked to a Picture Archiving and Communication System (PACS) 224. In a typical implementation, a PACS 224 may be linked to a remote system such as a radiology department information system, hospital information system, and/or internal or external network (not shown).

The computer 216 supplies commands to a table motor controller 118 to control the table 116. The table motor controller 118 can control the table motor so as to move the table 116 based on the instructions received. For example, the table motor controller 118 can move the table 116 so that the subject body 112 is positioned appropriately for imaging.

As mentioned above, the DAS 214 samples and digitally converts the projection data acquired by the detector elements 202. The image reconstruction unit 230 then reconstructs the image using the sampled and digitally converted data. The image reconstruction unit 230 includes one or a plurality of processors, which can perform the image reconstruction process. In FIG. 2, the image reconstruction unit 230 is illustrated as a separate structural element from the computer 216, but the image reconstruction unit 230 may form a part of the computer 216. In addition, the computer 216 may also perform one or more functions of the image reconstruction unit 230. Furthermore, the image reconstruction unit 230 may be located away from the CT system 100 and operatively connected to the CT device 100 using a wired or wireless network. The computer 216 and image reconstruction unit 230 function as image generation devices.

The image reconstruction unit 230 can store the reconstructed image in the storing device 218. The image reconstruction unit 230 may also transmit the reconstructed image to the computer 216. The computer 216 can transmit the reconstructed image and/or patient information to a display device 232 communicatively linked to the computer 216 and/or image reconstruction unit 230.

The various methods and processes described in the present specification can be stored as executable instructions on a non-transitory storage medium within the CT device 100. The executable instructions may be stored on a single storage medium or distributed across a plurality of storage media. One or more processors provided in the CT device 100 execute the various methods, steps, and processes described in the present specifications in accordance with instructions stored on a storage medium.

A camera 235 is provided on a ceiling 124 of the scan room 122 as an optical image acquisition unit for acquiring an optical image in the scan room. Any device can be used as the optical image acquisition unit as long as it can image the surface of a subject such as a subject body. For example, a camera that uses visible light for imaging the subject, a camera that uses infrared for imaging the subject, or a depth sensor that uses infrared to acquire depth data of the subject and performs imaging of the surface of the subject based on the depth data, can be used as the optical image acquisition unit. Also, the optical image acquired by the optical image acquisition unit may be a 3D image or a 2D image. Furthermore, the optical image acquisition unit may acquire the optical image as a still image or as video.

The CT device 100 is configured as described above. A flow of imaging a subject body using the CT device of Embodiment 1 will be described below. In the following example, in order to clarify the effect of Embodiment 1, first, a flow when examining a subject body using a general method will be described. Furthermore, after clarifying the problems of the general method, the flow of Embodiment 1 will be described.

Figure 3:
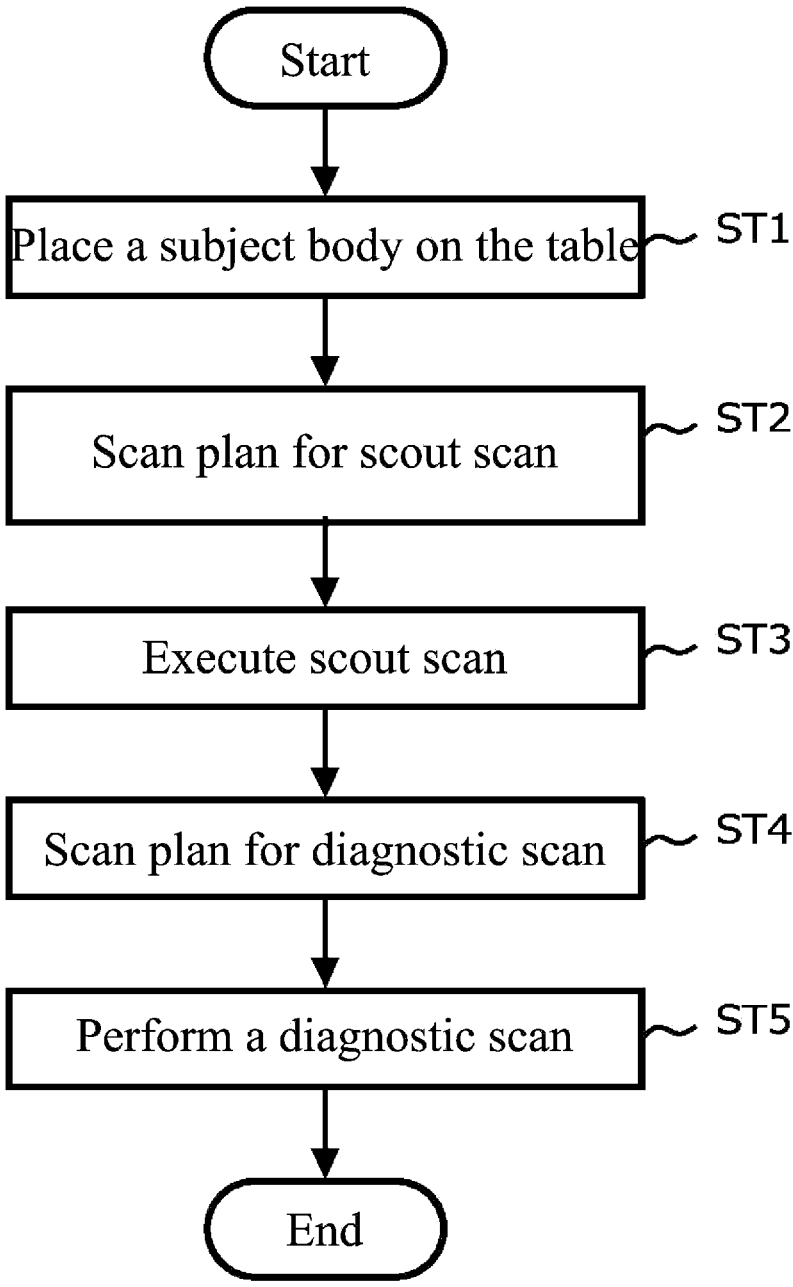
FIG. 3 is a diagram illustrating an example of the CT device operation flow when a subject body is examined using a general method.

FIG. 3 is a diagram illustrating an example of the CT device operation flow when a subject body is examined using a general method. At step ST1, the operator lays the subject body 112 (for example, a patient) on the table 116.

Figure 4:
FIG. 4 is a diagram illustrating a subject body 112 lying on a table 116.
Figure 4:
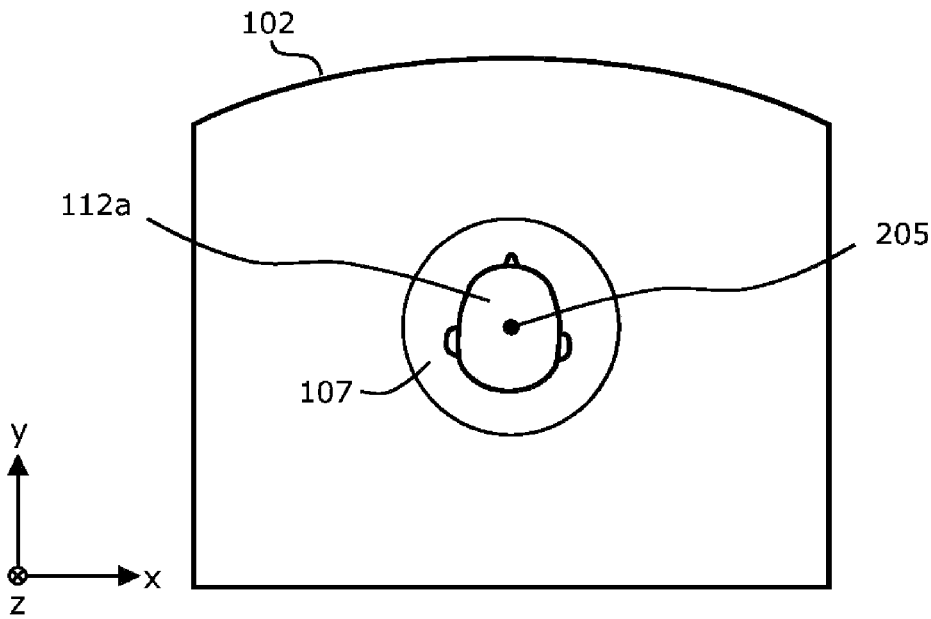
Figure 4:
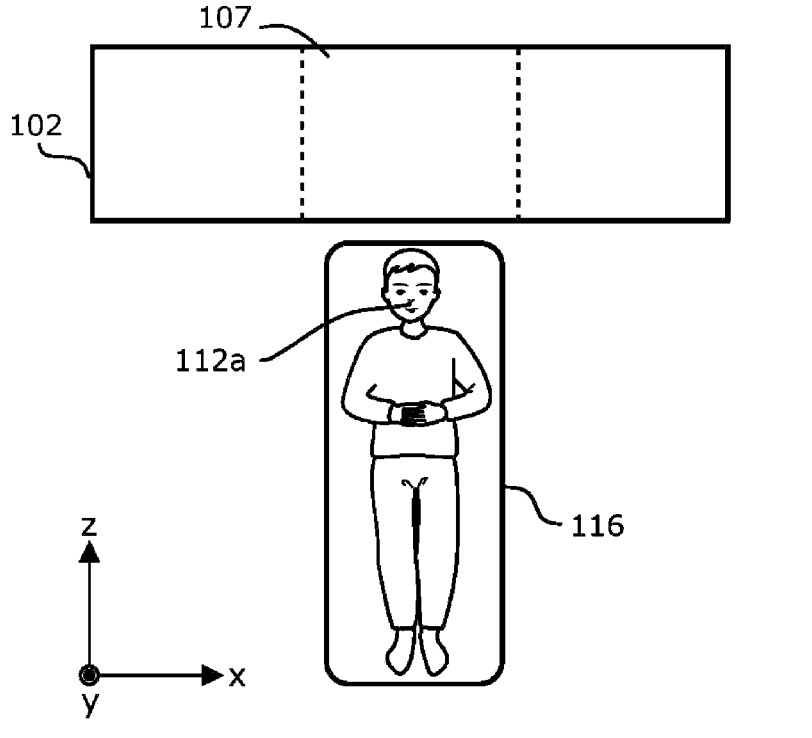

FIG. 4 is a diagram illustrating the subject body 112 lying on the table 116. A front view of the gantry 102 is shown in the upper part of FIG. 4, and a top view of the gantry 102 and of the table 116 is shown in the lower part of FIG. 4 The table 116 has a cradle on which the subject body 112 can lie. The cradle is configured so as to be movable in the axial direction (z direction). Note that the front view of the gantry 102 on the upper side of FIG. 4 illustrates the head 112a of the subject body 112 with respect to the opening 107 of the gantry 102 in the XY plane. Here, the imaging portion is assumed to be the head 112a. At step ST2, the operator establishes a scan plan for the scout scan.

Figure 5:
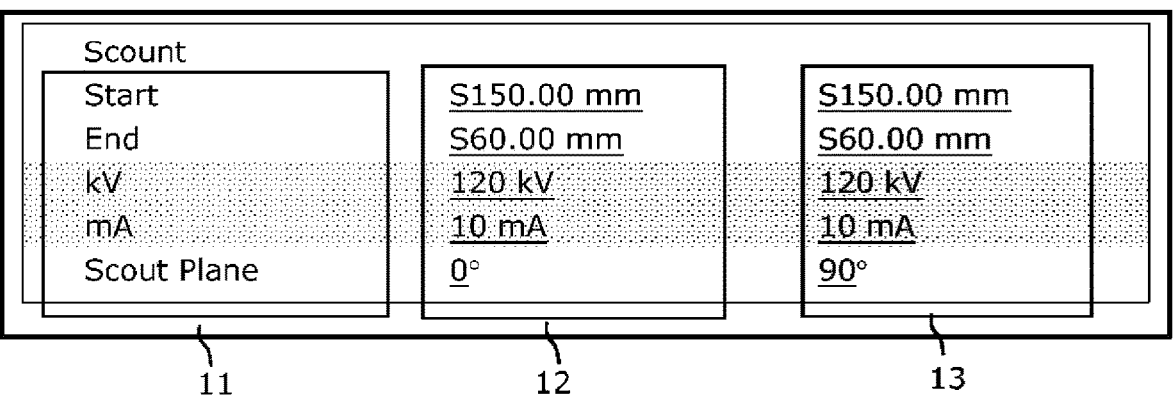
FIG. 5 is an explanatory diagram of an example of a scan plan for a scout scan.

FIG. 5 is an explanatory diagram of an example of a scan plan for a scout scan. FIG. 5 includes an item 11 required in the scout scan plan and scan plans 12 and 13 set for that item. In FIG. 5, "Start", "End", "kV", "mA", and "Scout Plane" are shown as items 11 of the scout scan plan. "Start" is the scan start position, "End" is the scan end position, "kV" is the tube voltage, "mA" is the tube current, and "Scout Plane" indicates the position of the X-ray tube 104 when the scout scan is executed. When the scout scan is ready, the process proceeds to step ST3. At step ST3, a scout scan is executed according to scan plans 12 and 13.

Figure 6:
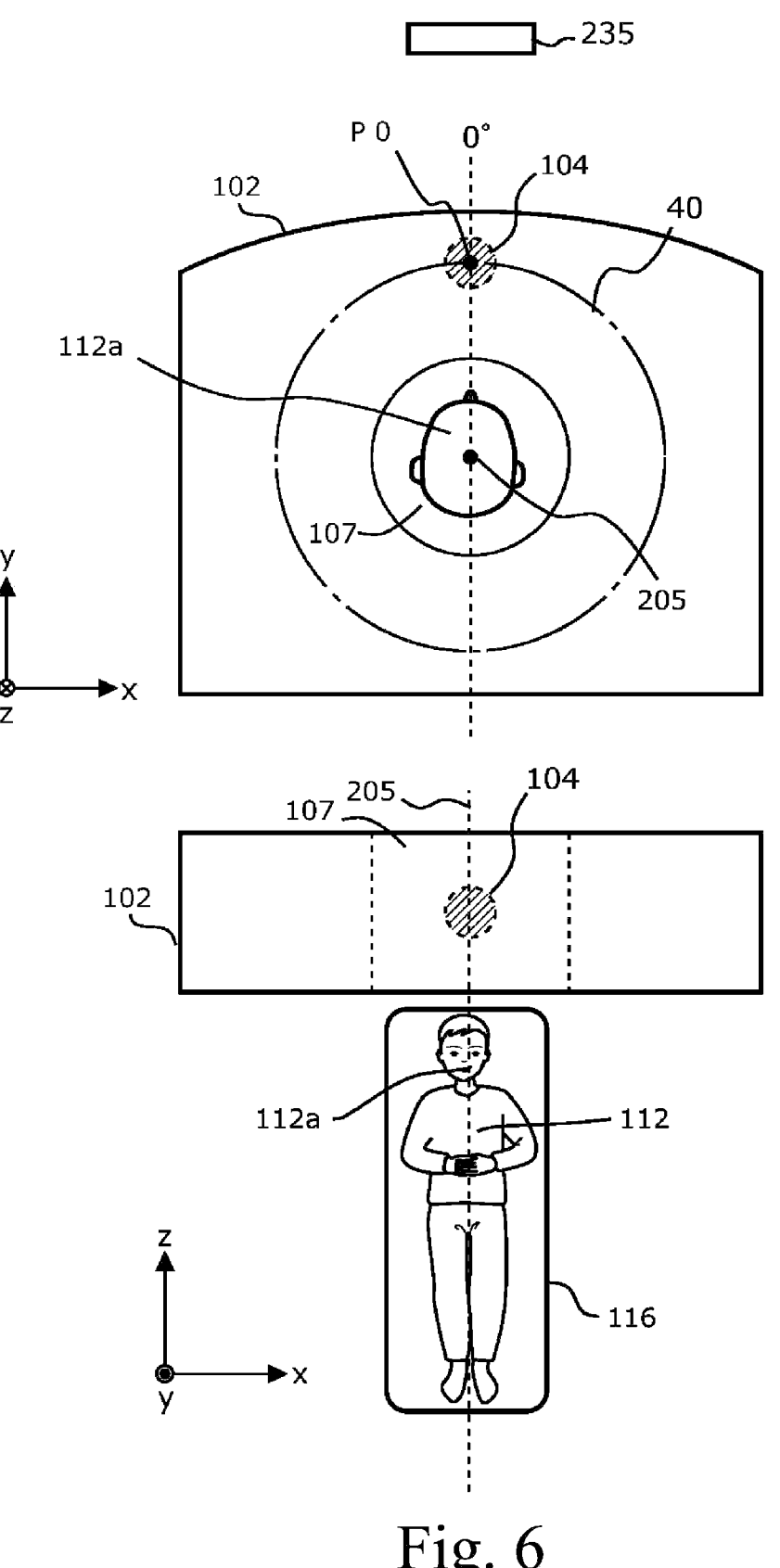
FIG. 6 is an explanatory diagram of a scout scan executed according to the scan plan 12.

FIG. 6 is an explanatory diagram of a scout scan executed according to the scan plan 12. The gantry 102 includes an x-ray tube 104. The X-ray tube 104 is configured to be rotatable on a path 40 centered on the rotation axis 205 within the XY plane. The rotation axis 205 may be set so as to coincide with the isocenter, or may be set as the rotation axis 205 at a position deviated from the isocenter. In the scan plan 12, "Scout Plane" is set to "0°". This indicates that the scout scan is executed with the X-ray tube 104 positioned at position P0 on the path 40, just above the rotation axis 205. Here, the angle of the X-ray tube 104 is assumed to be "0°" when the X-ray tube 104 is positioned at the position P0.

Figure 7:
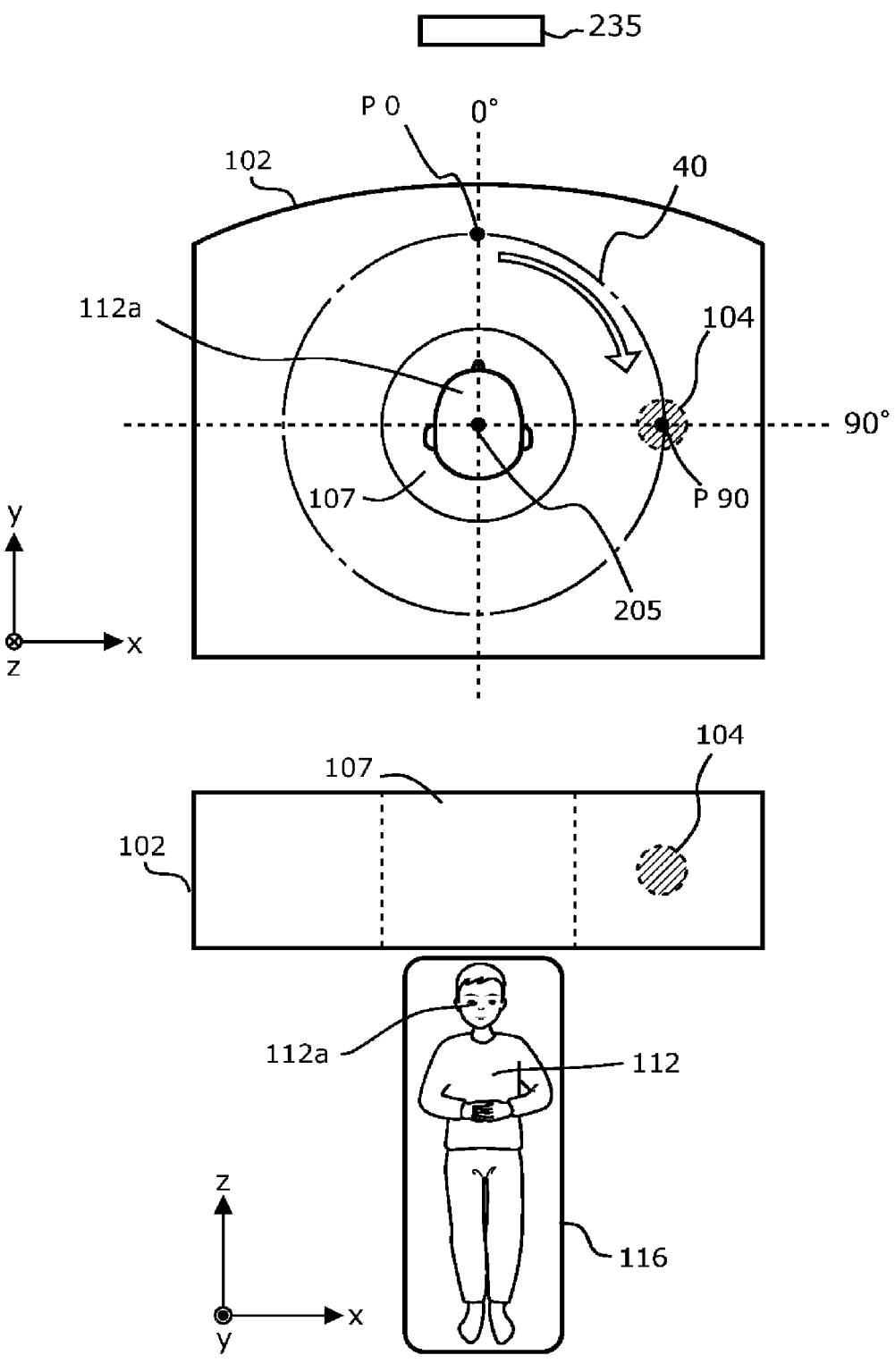
FIG. 7 is an explanatory diagram of a scout scan executed according to the scan plan 13.

FIG. 7 is an explanatory diagram of a scout scan executed according to the scan plan 13. The scan plan 13 has the "Scout Plane" set to "90°". This indicates that the scout scan is performed with the x-ray tube 104 positioned at position P90, which is a clockwise rotation of 90° from position P0 (angle 0°) around the rotation axis 205 on the path 40, as illustrated in FIG. 7. This assumes that the angle of the X-ray tube 104 is "90°" when the X-ray tube 104 is positioned at a position rotated clockwise by 90° from the angle of 0°.

When performing a scout scan, first, a scout scan is executed according to the scan plan 12. When performing the scout scan according to the scan plan 12, the gantry motor controller 212 (see FIG. 2) controls the gantry motor so that the X-ray tube 104 is positioned at angle 0° (position P0), as illustrated in FIG. 6. Furthermore, while moving the cradle in the Z-direction, the X-ray controller 210 controls the X-ray tube 104 so as to irradiate X-rays.

The X-ray detector 108 detects X-rays irradiated from the X-ray tube 104 and passed through the subject body 112. The projection data detected by the X-ray detector 108 is collected by the DAS 214. The DAS 214 performs prescribed processing, including sampling, digital conversion, and the like, on the acquired projection data and transmits the data to the computer 216 or image reconstruction unit 230. On the computer 216 or image reconstruction unit 230, a processor reconstructs the scout image based on the data obtained from the scan.

After executing a scout scan according to the scan plan 12, a scout scan is executed according to the scan plan 13. When performing a scout scan according to the scan plan 13, the gantry motor controller 212 controls the gantry motor so that the X-ray tube 104 rotates from a to 90° angle, as illustrated in FIG. 7. Therefore, the X-ray tube 104 is positioned at an angle of (position P90). Furthermore, while moving the cradle in the Z-direction, the X-ray tube 104 irradiates X-rays while positioned at an angle of 90°.

The X-ray detector 108 detects X-rays irradiated from the X-ray tube 104 and passed through the subject body 112. The projection data detected by the X-ray detector 108 is collected by the DAS 214. The DAS 214 performs prescribed processing, including sampling, digital conversion, and the like, on the acquired projection data and transmits the data to the computer 216 or image reconstruction unit 230. On the computer 216 or image reconstruction unit 230, a processor reconstructs the scout image based on the data obtained from the scan.

Figure 8:
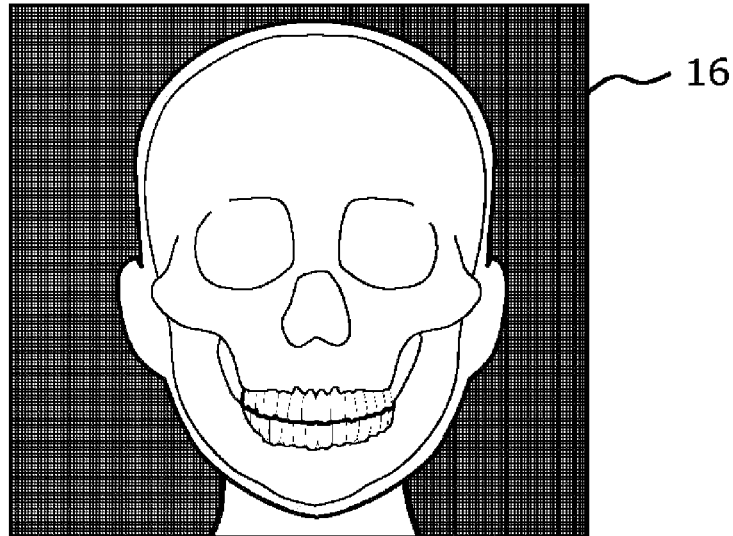
FIG. 8 is a schematic view of scout images 16 and 17.
Figure 8:
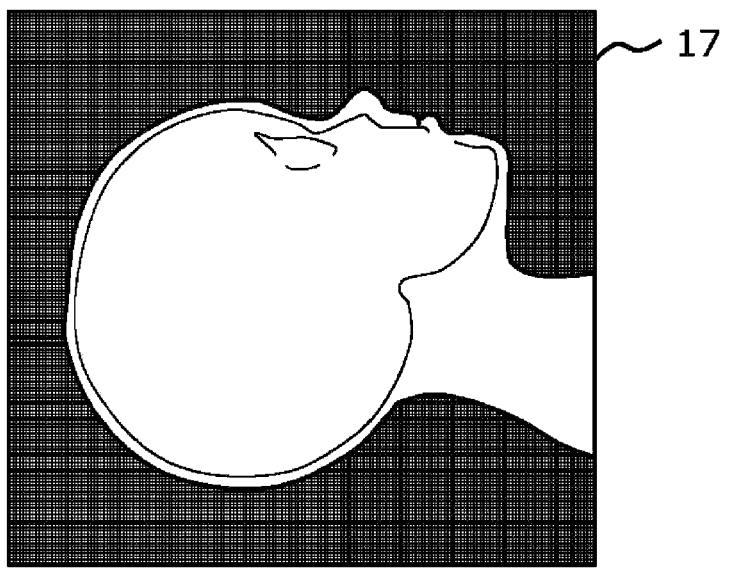

Therefore, a scout image when the scan plan 12 is executed and a scout image when the scan plan 13 is executed can be obtained. FIG. 8 schematically shows the scout image 16 when the scan plan 12 is executed and a scout image 17 when the scan plan 13 is executed. The scout image 16 is an image obtained by irradiating X-rays from the X-ray tube 104 positioned at an angle of 0° (position P0), and the scout image 17 is an image obtained by irradiating X-rays from the X-ray tube 104 positioned at an angle of 90° (position P90). After executing the scout scan, the process proceeds to step ST4.

At step ST4, the operator makes a scan plan for a diagnostic scan. The operator, for example, refers to the scout images 16 and 17 (see FIG. 8) to set the scan range for the diagnostic scan, which will be described later. The computer 216 also executes various processes based on the scout images 16 and 17. For example, if Organ Dose Modulation (ODM) is used, that is a dose reduction technique used during diagnostic scans, the computer 216 executes processing to segment the scout images 16 and 17 and identify organs (for example, the eye) that are highly sensitive to radiation within the imaging portion that is the head 112a based on the segmentation results. When the preparation for executing the diagnostic scan is complete, processing proceeds to step ST5.

Figure 9:
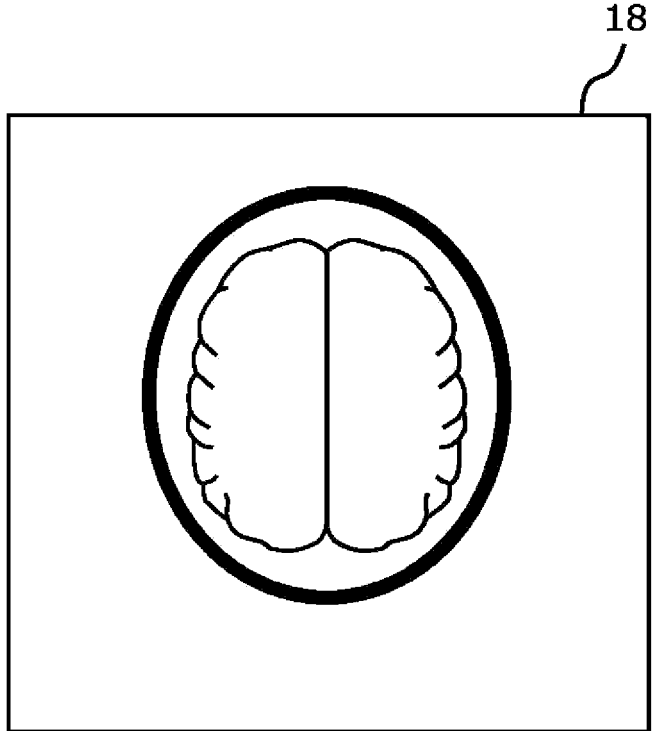
FIG. 9 is a diagram illustrating an example of a CT image 18 displayed on a display device 232.

At step ST5, a diagnostic scan of the head 112a is performed. For example, when executing a diagnostic scan using ODM, a scan of the head 112a is executed so that the exposure of the radiation-sensitive eyes is selectively reduced. The X-ray detector 108 detects X-rays irradiated from the X-ray tube 104 and that pass through the subject body 112. The projection data detected by the X-ray detector 108 is collected by the DAS 214. The DAS 214 performs prescribed processing, including sampling, digital conversion, and the like, on the acquired projection data and transmits the data to the computer 216 or image reconstruction unit 230. In the computer 216 or image reconstruction unit 230, a processor reconstructs a CT image necessary for diagnosis of the head 112a of the subject body 112 based on data obtained from the diagnostic scan. The operator can display the reconstructed CT image on the display device 232. FIG. 9 is a diagram illustrating an example of the CT image 18 displayed on the display device 232. Thus, the examination flow is complete.

A doctor can interpret the CT images acquired according to the examination flow and perform a diagnosis. In the above description, as illustrated in FIG. 6 and FIG. 7, scanning is performed with the subject body 112 lying on the table 116 with the face of the subject facing upward. However, depending on the subject body 112, facing directly upward may not be possible. For example, if facing the face of the subject body directly upward is not possible because the subject body 112 is elderly or suffering from illness, the face of the subject body 112 may face, for example, obliquely upward (see FIG. 10 and FIG. 11).

Figure 10:
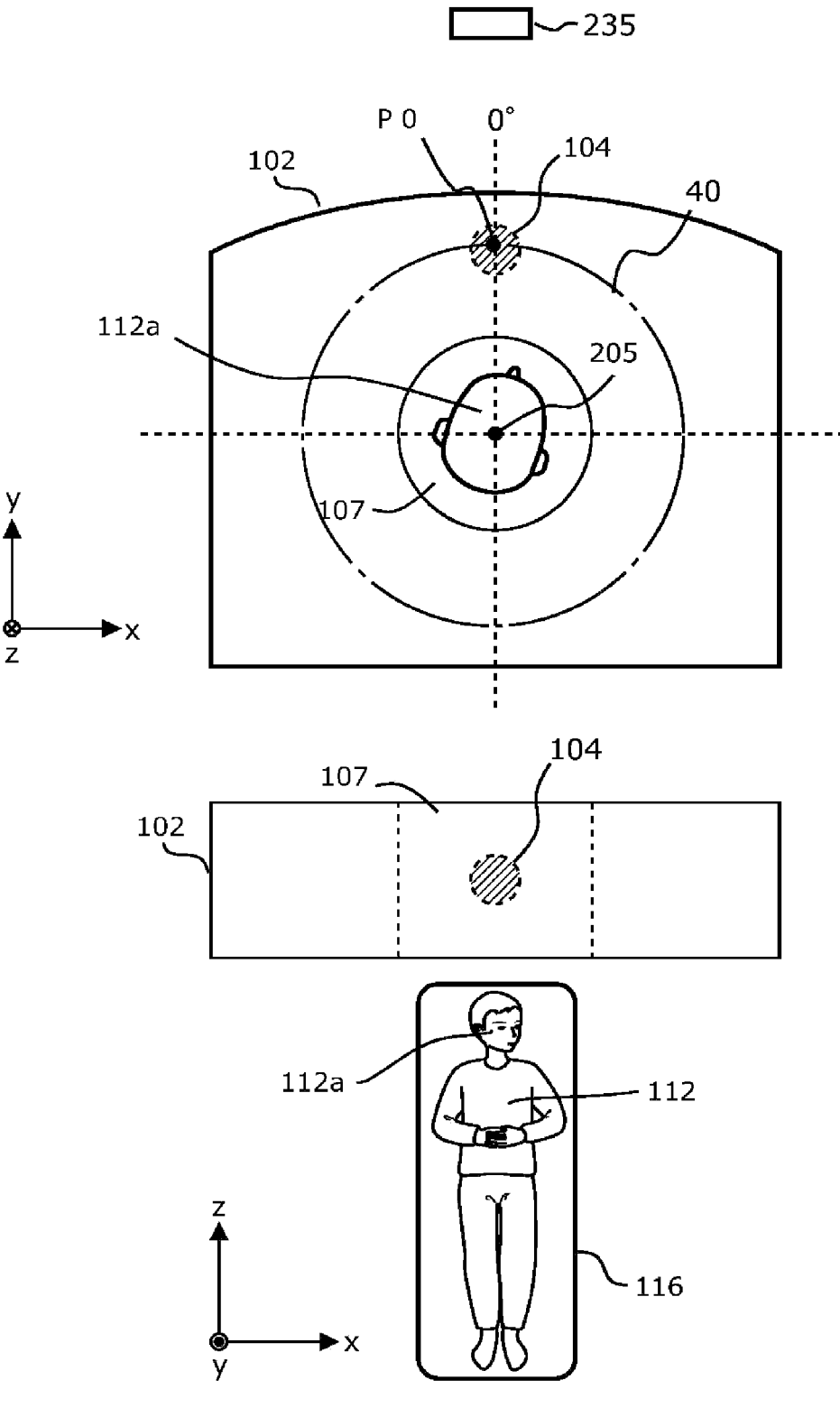
FIG. 10 is a front view and a top view of the gantry 102.
Figure 11:
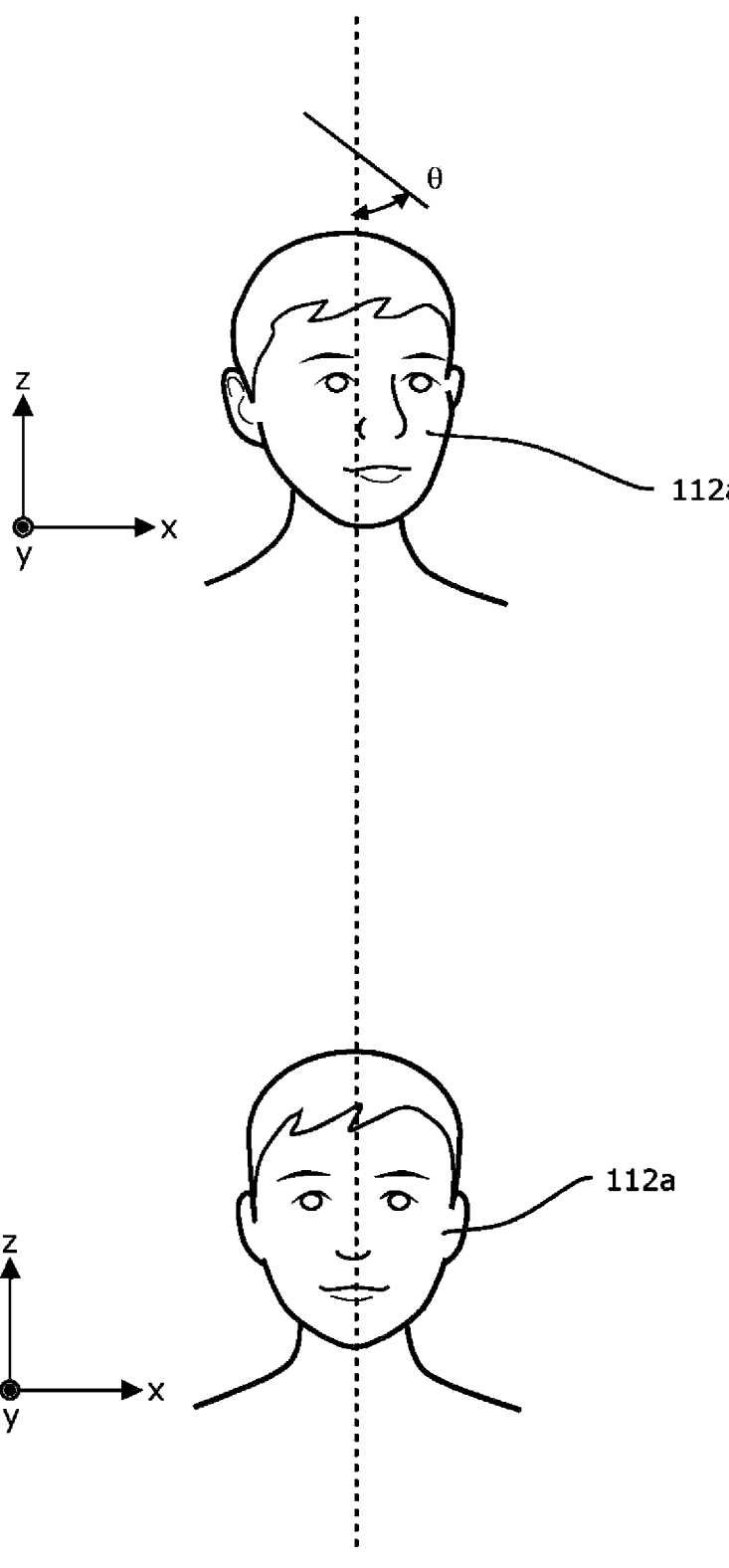
FIG. 11 illustrates an enlarged view of the head of the subject body 112.

FIG. 10 and FIG. 11 are diagrams illustrating examples in which the face of the subject body 112 cannot face directly upward. A front view of the gantry 102 is illustrated in the upper part of FIG. 10, and a top view of the gantry 102 and the table 116 are shown in the lower part of FIG. 10. The subject body 112 lies on the table 116. Note that the front view of the gantry 102 on the upper side of FIG. 10 illustrates the head 112a of the subject body 112 with respect to the opening 107 of the gantry 102 in the XY plane.

In addition, FIG. 11 illustrates an enlarged view of the head of the subject body 112. FIG. 11 illustrates the head 112a in a state in which the subject body 112 cannot face directly upward and faces obliquely upward. Note that for reference, the lower side of FIG. 11 illustrates the head 112a of the subject body 112 facing upward. The subject body 112 is lying on a table with the head rotated by an angle θ from a state of facing straight up.

Figure 12:
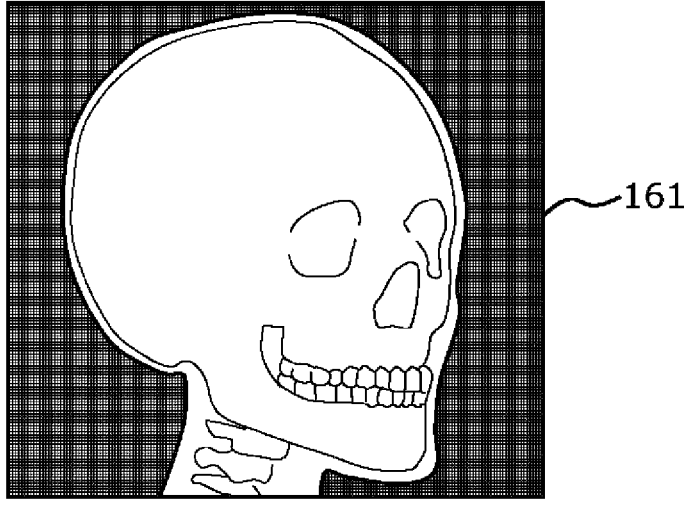
FIG. 12 is a diagram illustrating scout images 161 and 171 in a state where the face of a subject body 112 is oriented obliquely.
Figure 12:
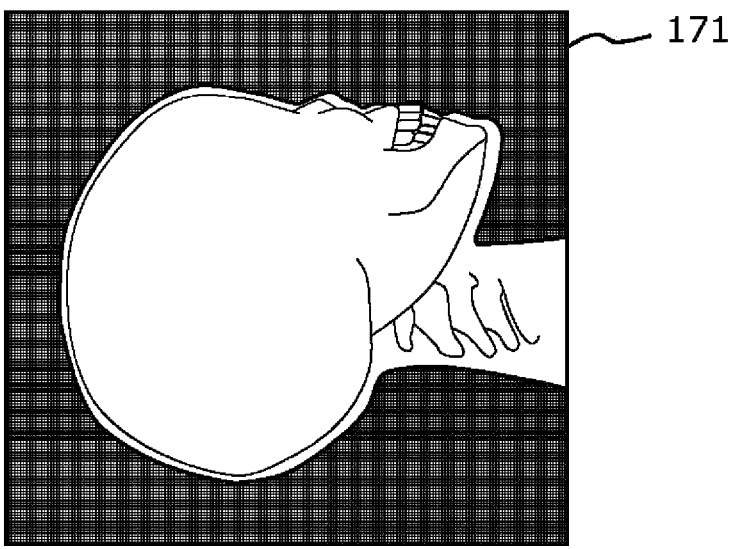
Figure 13:
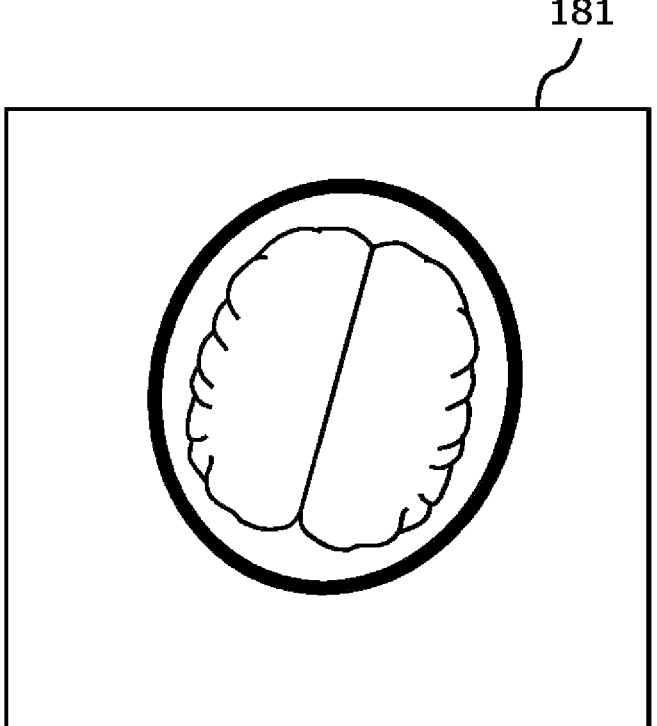
FIG. 13 is a diagram illustrating a CT image 181 in a state in which the face of a subject body 112 faces obliquely upward.

In this case, since the face of the subject body 112 cannot be forcibly caused to face directly upward, scanning is performed with the face of the subject body 112 facing obliquely upward. Therefore, when a scout scan is executed, scout images 161 and 171 are obtained with the face of the subject body 112 obliquely oriented, as illustrated in FIG. 12. Therefore, the processor executes segmentation based on the scout images 161 and 171 with the face of the subject body 112 obliquely oriented. However, if the segmentation is executed based on a scout image in which the face of the subject body 112 is oriented obliquely, there is a problem that the accuracy of the segmentation is lowered. For this reason, in step ST4, when the processor executes processing for identifying organs (for example, eyes) that are highly sensitive to radiation based on the scout images 161 and 171, the detection accuracy of the organs becomes low. Consequently, selectively reducing eye exposure in diagnostic scans becomes difficult. In addition, since the diagnostic scan is executed with the face of the subject body 112 obliquely oriented, when the CT image obtained by the diagnostic scan is displayed on the display device 232, the CT image 181 is displayed as in FIG. 13 with the face of the subject body 112 facing obliquely upward. Therefore, the doctor must perform a diagnosis of the subject body 112 while viewing the CT image 181 acquired with the face of the subject body 112 obliquely oriented. However, in imaging in the supine position, the face of the subject body 112 generally faces directly upward. Therefore, when diagnosing the head 112a based on the CT image 181 acquired with the face of the subject body 112 obliquely oriented, the doctor may find that the orientation of the face of the subject body 112 is different from the normal orientation causing an increase in the burden on the doctor during diagnosis.

Figure 14:
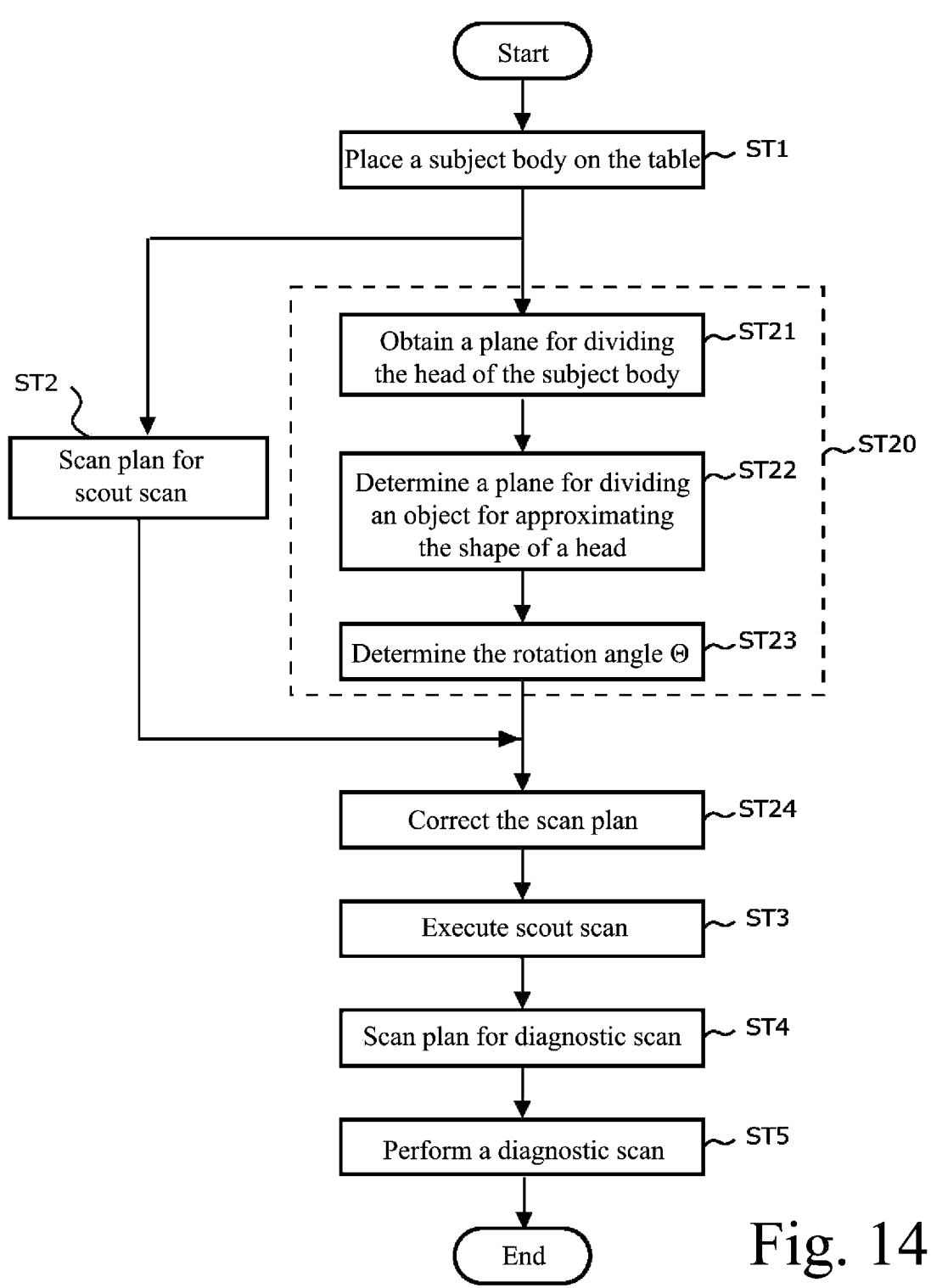
FIG. 14 is a diagram illustrating CT device operation flow when the subject body 112 is imaged in Embodiment 1.

Therefore, the CT device in Embodiment 1 is configured so as to be able to cope with the problem described above. The CT device of Embodiment 1 will be described below. FIG. 14 is a diagram illustrating CT device operation flow when the subject body 112 is imaged in Embodiment 1. Note that in executing the flow indicated in FIG. 14, some steps can be omitted or added, some steps can be divided into a plurality of steps, some steps can be executed in a different order, and some steps can be repeated.

In step ST1, the operator calls the subject body 112 into the scan room and lays the subject body 112 on the table 116. Here, as illustrated in FIG. 10 and FIG. 11, it is assumed that the face of the subject body 112 can not face directly upwards and so is obliquely oriented.

The camera 235 starts imaging in the scan room 122 before the subject body 112 enters the scan room 122. Signals captured by camera 235 are sent to the computer 216. The computer 216 generates camera images based on signals received from the camera 235. Therefore, the camera image of the subject in the scan room 122 can be generated before the subject body 112 enters the scan room 122.

The field of view of the camera 235 includes the table 116 and the surrounding area thereof. Therefore, when the subject body 112 lies on the table 116, the computer can generate a camera image of subject body 112 lying on table 116 based on signals from the camera 235. Camera images are stored in the storing device 218.

At step ST2, the operator establishes a scan plan for the scout scan. On the other hand, in step ST20, the computer 216 recognizes each portion (head, chest, abdomen, upper limbs, lower limbs, and the like) of the subject body 112 and the position of each portion based on the camera image, and the orientation of the portion of the subject body 112 on the table 116 to be imaged is determined. Here, the portion of the subject body 112 to be imaged is the head 112*a*. Therefore, the processor determines the orientation of the head 112*a* of the subject body 112. The flow of step ST20 will be described in detail below with reference to FIG. 15 to FIG. 17.

Figure 15:
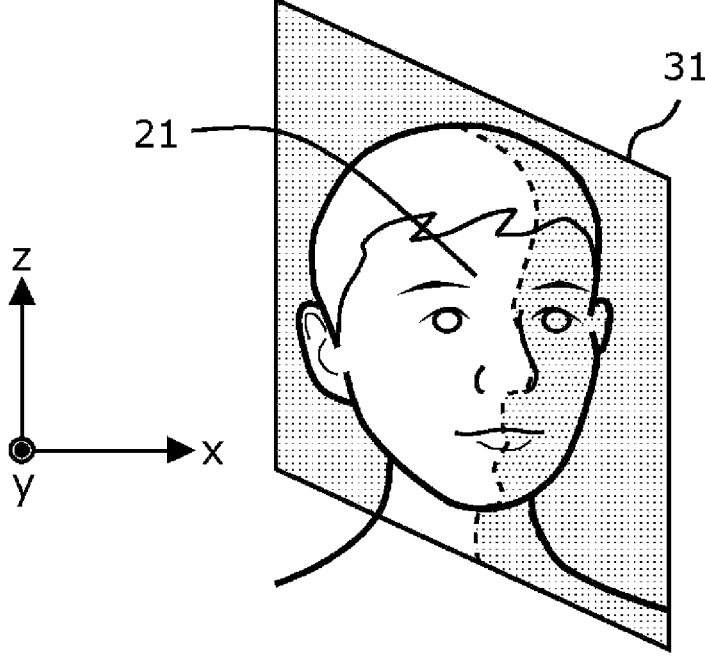
FIG. 15 is a diagram illustrating a central plane 31 dividing a head 112a of the subject body 112 into left and right.

In step ST21, the computer 216 sets the central plane 31 that divides the head of the subject body 112 into left and right, based on the camera image 21 of the subject body 112, as illustrated in FIG. 15. For example, the computer 216 extracts a plurality of characteristic points (for example, eyebrows, eyes, nose, mouth, chin) on the surface of the face of the subject body 112 based on the camera image 21, and based on the extracted characteristic points, the central plane 31 that divides the head 112*a* of the subject 112 into left and right can be determined.

Figure 16:
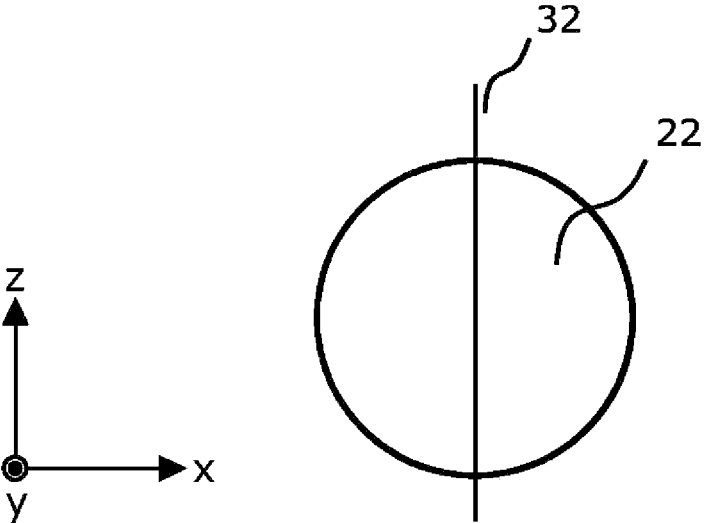
FIG. 16 is a diagram illustrating an object 22 approximating the head 112a of the subject body 112 and a reference plane 32 dividing the object 22 into two.

In step ST22, the computer 216 approximates the head of the subject body 112 as an object 22 (for example, sphere, ellipsoid) having a symmetrical shape with respect to the YZ plane, as illustrated in FIG. 16, and obtains the reference plane 32 that divides the object 22 in two in the X direction. The reference plane 32 is a plane parallel to the YZ plane. Therefore, the reference plane 32 approximates a plane that divides the face of the subject body 112 into left and right when the face of the subject body 112 is assumed to face an ideal direction suitable for examination (that is, in the Y direction). After determining the reference plane 32, processing proceeds to step ST23.

Figure 17:
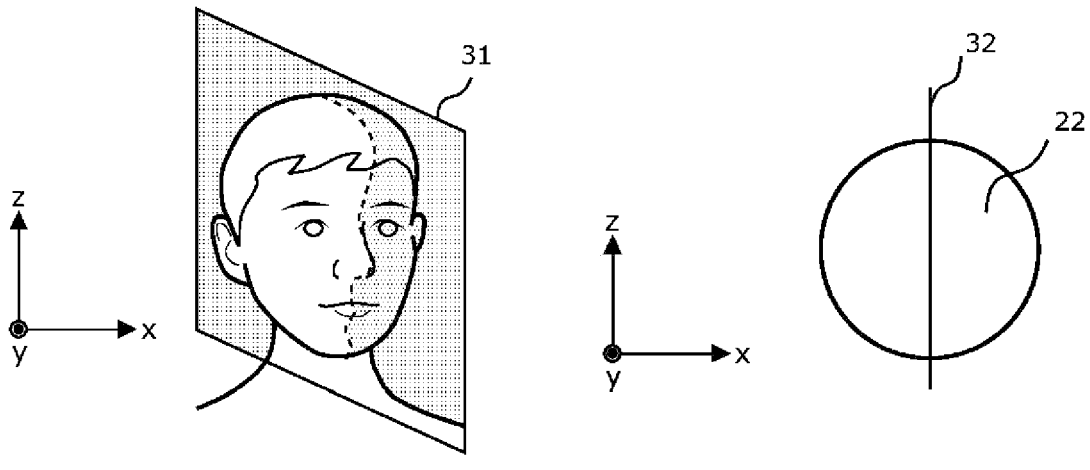
FIG. 17 is an explanatory diagram of a method of obtaining a rotation angle θ of the head of the subject body.
Figure 17:
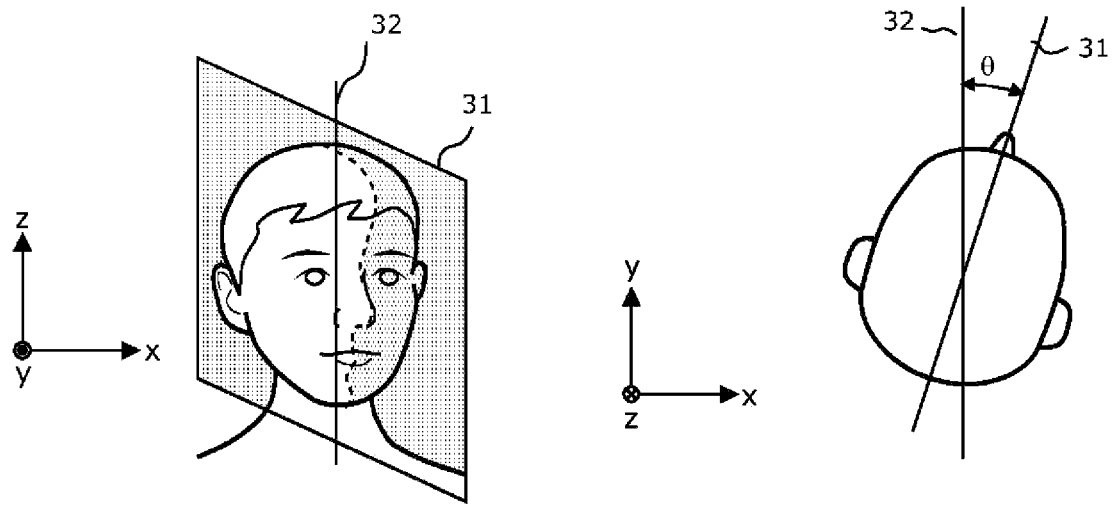

In step ST23, the computer 216 obtains the rotation angle θ of the head of the subject body based on the central plane 31 and the reference plane 32. FIG. 17 is an explanatory diagram of a method of obtaining a rotation angle θ of the head of the subject body. The upper left of FIG. 17 illustrates the central plane 31 obtained in step ST21, and the upper right of FIG. 17 illustrates the reference plane 32 obtained in step ST22. In addition, FIG. 17 illustrates the central plane 31 and the reference plane 32 as viewed from the Y direction, and the lower right of FIG. 17 illustrates the center plane 31 and the reference plane 32 as viewed from the Z direction.

The reference plane 32 obtained in step ST22 approximates a plane that divides the face of the subject body 112 into left and right when the face of the subject body 112 is assumed to face an ideal direction suitable for examination (that is, the Y direction). Therefore, the angle θ between the central plane 31 and the reference plane 32 can be obtained as the rotation angle θ of the head 112*a* of the subject body 112. For example, when θ=0°, this indicates that the central plane 31 coincides with the reference plane 32, in other words, this indicates that the face of the subject body 112 faces the ideal direction (directly upward). Therefore, θ=0° means that the head 112*a* of the subject body 112 is not tilted. On the other hand, if θ>0°, this indicates that the central plane 31 does not coincide with the reference plane 32 and indicates that the direction of the face of the subject body 112 is rotated from the ideal direction (directly upward) by an angle around the body axis (Z-axis). Therefore, θ>0° means that the head 112*a* of the subject body 112 is tilted.

Thus, in step ST20, the rotation angle θ can be obtained as a value representing the orientation of the head 112*a* of the subject body 112. Here, it is assumed that θ=15°. After calculating the rotation angle θ, the process proceeds to step ST24.

Figure 18:
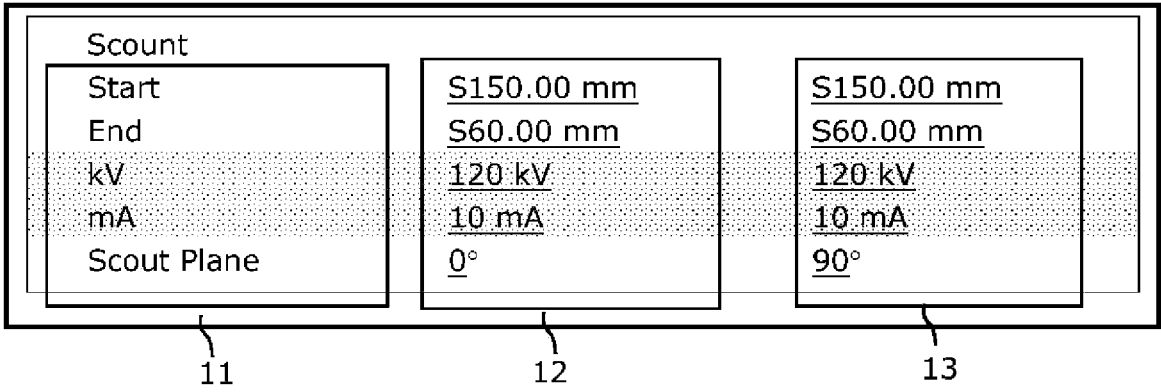
FIG. 18 is an explanatory diagram of an example of a scout scan plan after correction.
Figure 18:
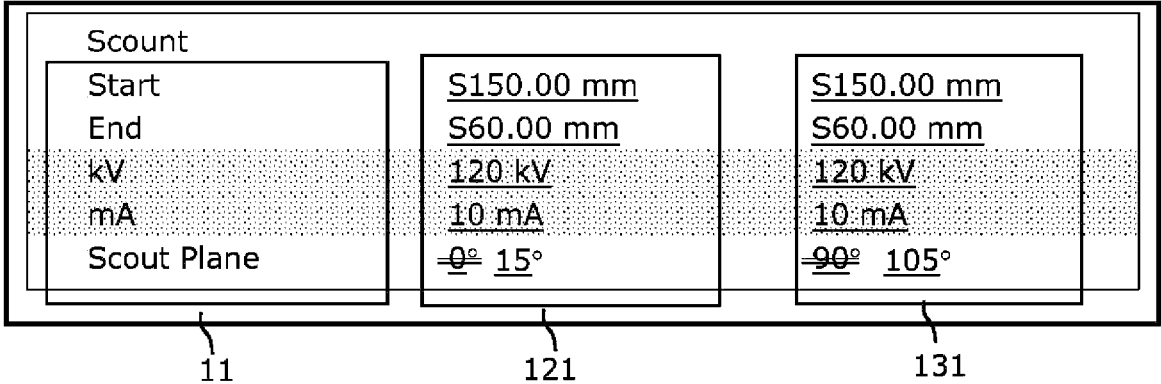
Figure 19:
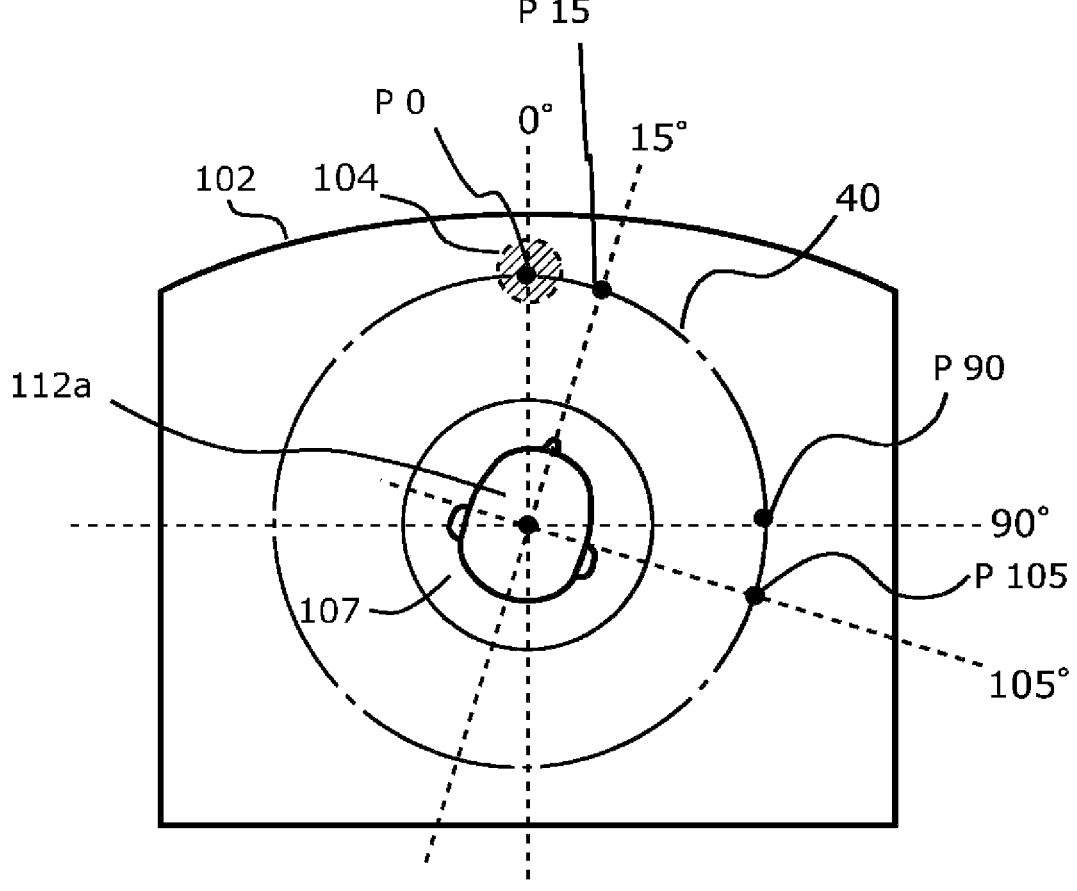
FIG. 19 is an explanatory diagram of "Scout Plane" included in a scan plan.

At step ST24, the computer 216 corrects the scan plan for the scout scan based on the rotation angle θ obtained in step ST20. FIG. 18 is an explanatory diagram of an example of a scout scan plan after correction. FIG. 19 is an explanatory diagram of the "Scout Plane" included in a scan plan. The top of FIG. 18 illustrates the scout scan plans 12 and 13 before correction, and the bottom of FIG. 18 illustrates the scout scan plans 121 and 131 after correction.

At step ST24, the computer 216 corrects the value of the item "Scout Plane" of the scan plans 12 and 13 based on the rotation angle θ (orientation of the portion to be imaged). The "Scout Plane" in the scout scan plan 12 before correction is set to an angle of "0°" corresponding to the initial position of the X-ray tube 104 and the "Scout Plane" in the scout scan plan 13 before correction is set to an angle of "90°" corresponding to the initial position of the X-ray tube 104.

In Embodiment 1, the rotation angle θ is calculated to be θ=15°, so the computer 216 corrects the value of the item "Scout Plane" in the scan plan 12 from 0° to 0°+15°=15° so that X-rays can be irradiated directly in front of the face of the subject body. In addition, the computer 216 corrects the value of the item "Scout Plane" of the scan plan 13 from 90° to 90°+15°=105° so that X-rays can be irradiated directly from the side of the face of the subject body. Therefore, the "Scout Plane" values of the scan plans 121 and 131 after correction are set to "15°" and "105°," respectively. "Scout Plane"=15° indicates that the X-ray tube 104 is arranged at a position P15 rotated clockwise by 15° from the position P0 (angle of 0°) on the path 40 as illustrated in FIG. 19. In addition, "Scout Plane"=105° indicates that the X-ray tube 104 is arranged at a position P105 rotated clockwise by 15° from the position P90 (angle of 90°) on the path 40 as illustrated in FIG. 19. Therefore, the computer 216 can determine two positions P15 and P105 on the path 40 where the X-ray tube 104 is positioned based on rotation angle θ

(based on head orientation). After correcting the scan plan, processing proceeds to step ST3.

Figure 20:
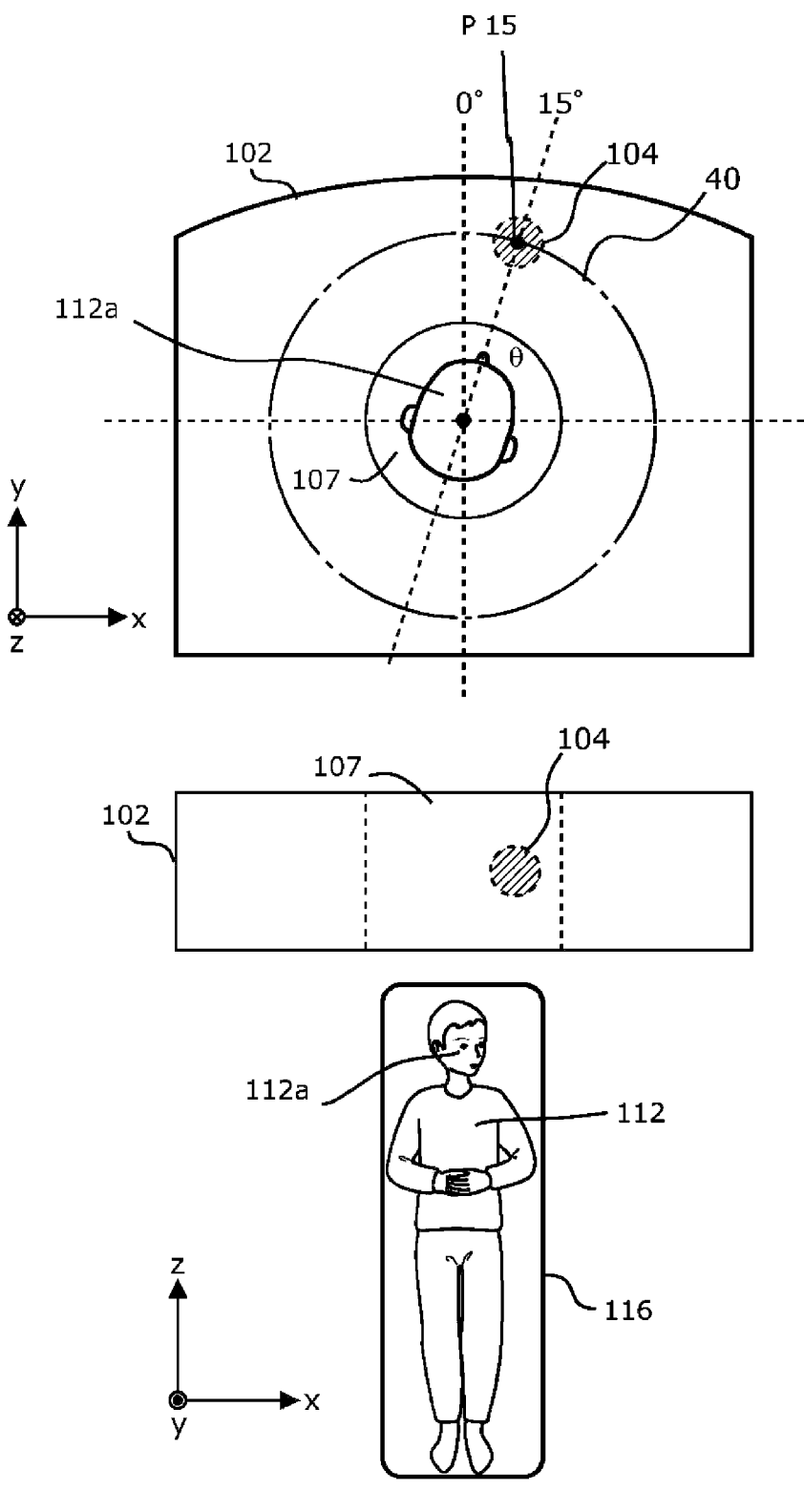
FIG. 20 is an explanatory diagram of the scout scan executed based on a corrected scout scan plan 121.

At step ST3, a scout scan is executed. The scout scan is executed based on the corrected scout scan plans 121 and 131 (see FIG. 18). In Embodiment 1, first, a scout scan is executed based on the scout scan plan 121 (see FIG. 20). FIG. 20 is an explanatory diagram of the scout scan executed based on a corrected scout scan plan 121.

When performing a scout scan based on the scout scan plan 121, the gantry motor controller 212 (see FIG. 2) controls the gantry motor so that the X-ray tube 104 is positioned at position P15 (angle 15°) on the path 40, rotated 15° clockwise from angle 0°. Next, the table motor controller 118 (see FIG. 2) then controls the table motor so as to move the cradle in the Z direction, while the X-ray controller 210 causes the X-ray tube 104 to irradiate X-rays.

The X-ray detector 108 detects X-rays irradiated from the X-ray tube 104 and that pass through the subject body 112. The projection data detected by the X-ray detector 108 is collected by the DAS 214. The DAS 214 performs prescribed processing, including sampling, digital conversion, and the like, on the acquired projection data and transmits the data to the computer 216 or image reconstruction unit 230. A processor in the computer 216 or image reconstruction unit 230 reconstructs a scout image based on data obtained from scans executed with the X-ray tube 104 positioned at an angle of 15°.

Figure 21:
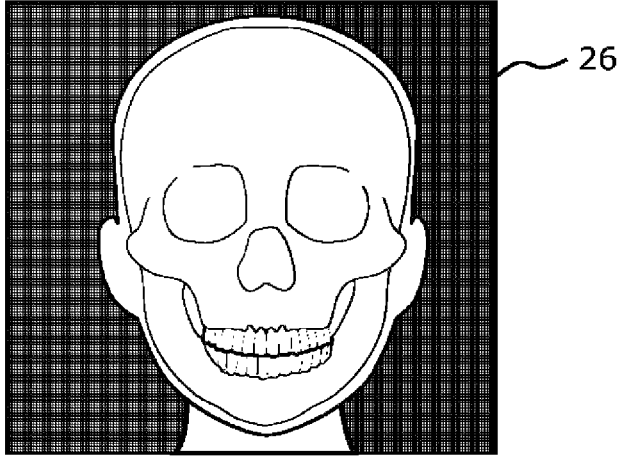
FIG. 21 is a diagram schematically illustrating a scout image 26 acquired in accordance with the scan plan 121.
Figure 21:
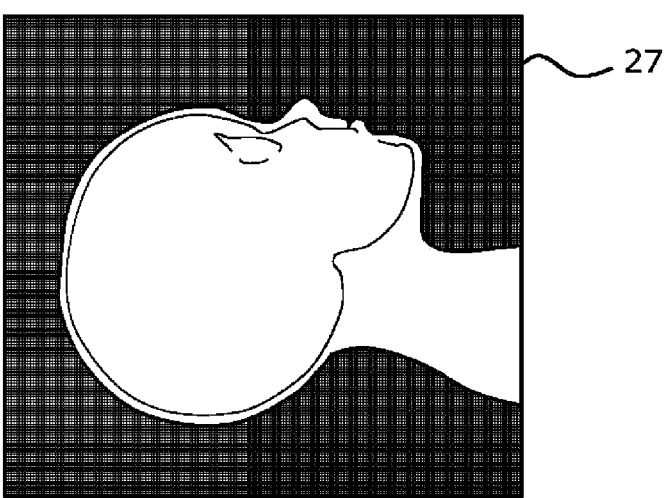

Therefore, when executing a scout scan according to the scan plan 121, the X-ray tube 104 can be positioned at an angle of 15° (position P15), as illustrated in FIG. 20, so that a scout image taken from directly in front of the face of the subject body 112 can be acquired. FIG. 21 schematically illustrates a scout image 26 acquired according to the scan plan 121.

Figure 22:
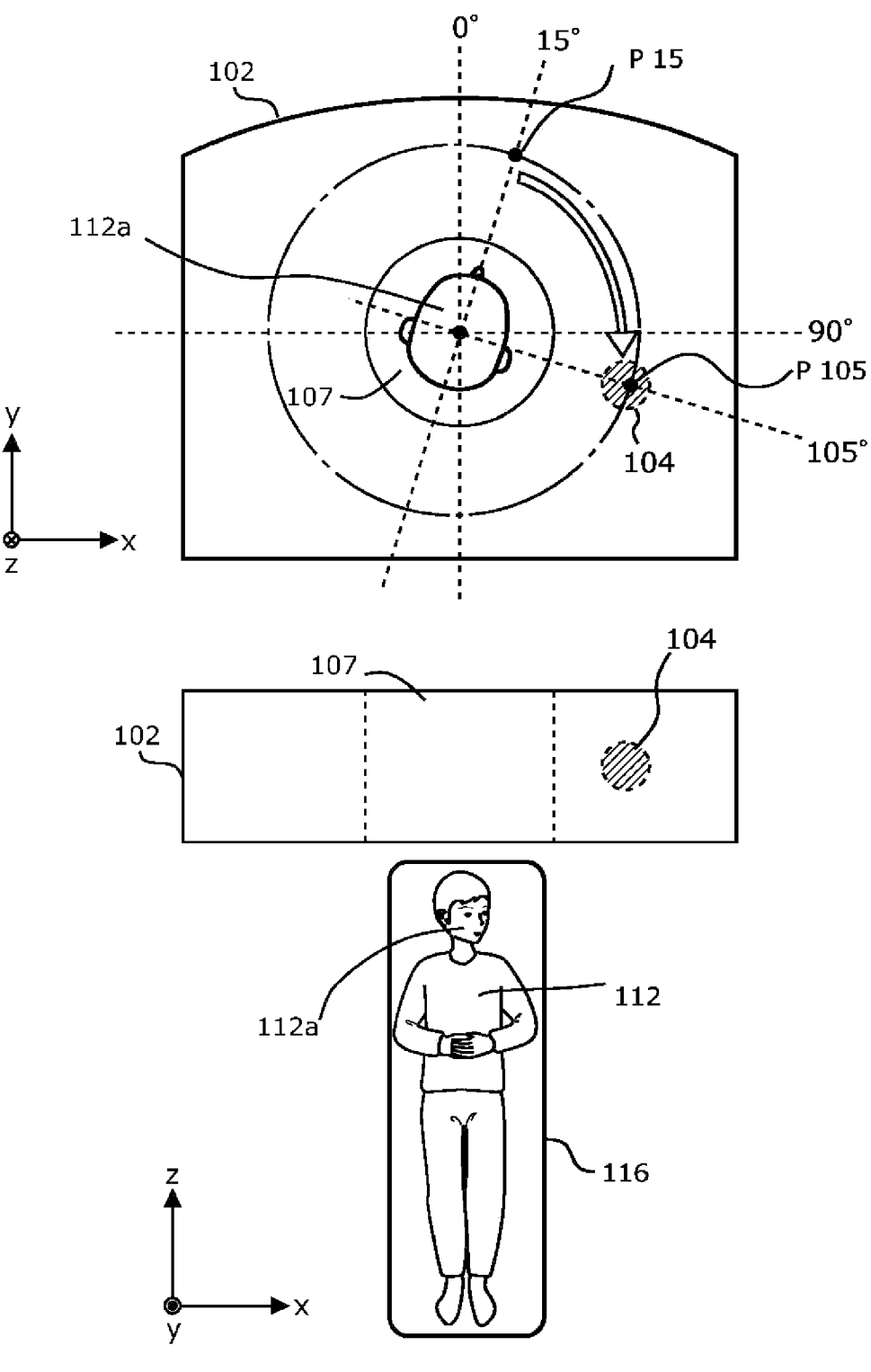
FIG. 22 is an explanatory diagram of the scout scan executed based on a corrected scout scan plan 131.

After executing a scout scan according to the scan plan 121, a scout scan is executed according to the scan plan 131. FIG. 22 is an explanatory diagram of the scout scan executed based on a corrected scout scan plan 131.

When performing a scout scan according to the scan plan 131, the gantry motor controller 212 controls the gantry motor so that the X-ray tube 104 rotates 90° from position P15 (angle 15°). Therefore, the X-ray tube 104 is positioned at a position of P105 (angle 105°). While the table motor controller 118 moves the cradle in the Z direction, the X-ray controller 210 causes the X-ray tube 104 to irradiate X-rays while the X-ray tube 104 is positioned at an angle of 105°.

The X-ray detector 108 detects X-rays irradiated from the X-ray tube 104 and that pass through the subject body 112. The projection data detected by the X-ray detector 108 is collected by the DAS 214. The DAS 214 performs prescribed processing, including sampling, digital conversion, and the like, on the acquired projection data and transmits the data to the computer 216 or image reconstruction unit 230. A processor in the computer 216 or image reconstruction unit 230 reconstructs a scout image based on data obtained from scans executed with the X-ray tube 104 positioned at an angle of 105°.

Therefore, when executing a scout scan according to the scan plan 131, the X-ray tube 104 can be positioned at an angle of 105° (position P105), as illustrated in FIG. 22, so that a scout image taken directly from the side of the head 112a of the subject body 112 can be acquired. FIG. 21 schematically illustrates a scout image 27 acquired in accordance with the scan plan 131.

After executing the scout scan, the process proceeds to step ST4. At step ST4, the operator makes a scan plan for a diagnostic scan. The operator, for example, refers to the scout images 26 and 27 to set the scan range for the diagnostic scan, which will be described later. The computer 216 also executes various processes based on the scout images 26 and 27. For example, in Embodiment 1, the computer 216 segments the scout images 26 and 27, and based on the results of the segmentation, processing that identifies organs of the head 112a that is the portion to be imaged with high sensitivity to radiation (for example, the eyes) is executed. Organs with high sensitivity to radiation can be identified using trained models created using AI techniques such as deep learning and machine learning. A method for identifying organs with high sensitivity to radiation using a trained model is described below.

Figure 23:
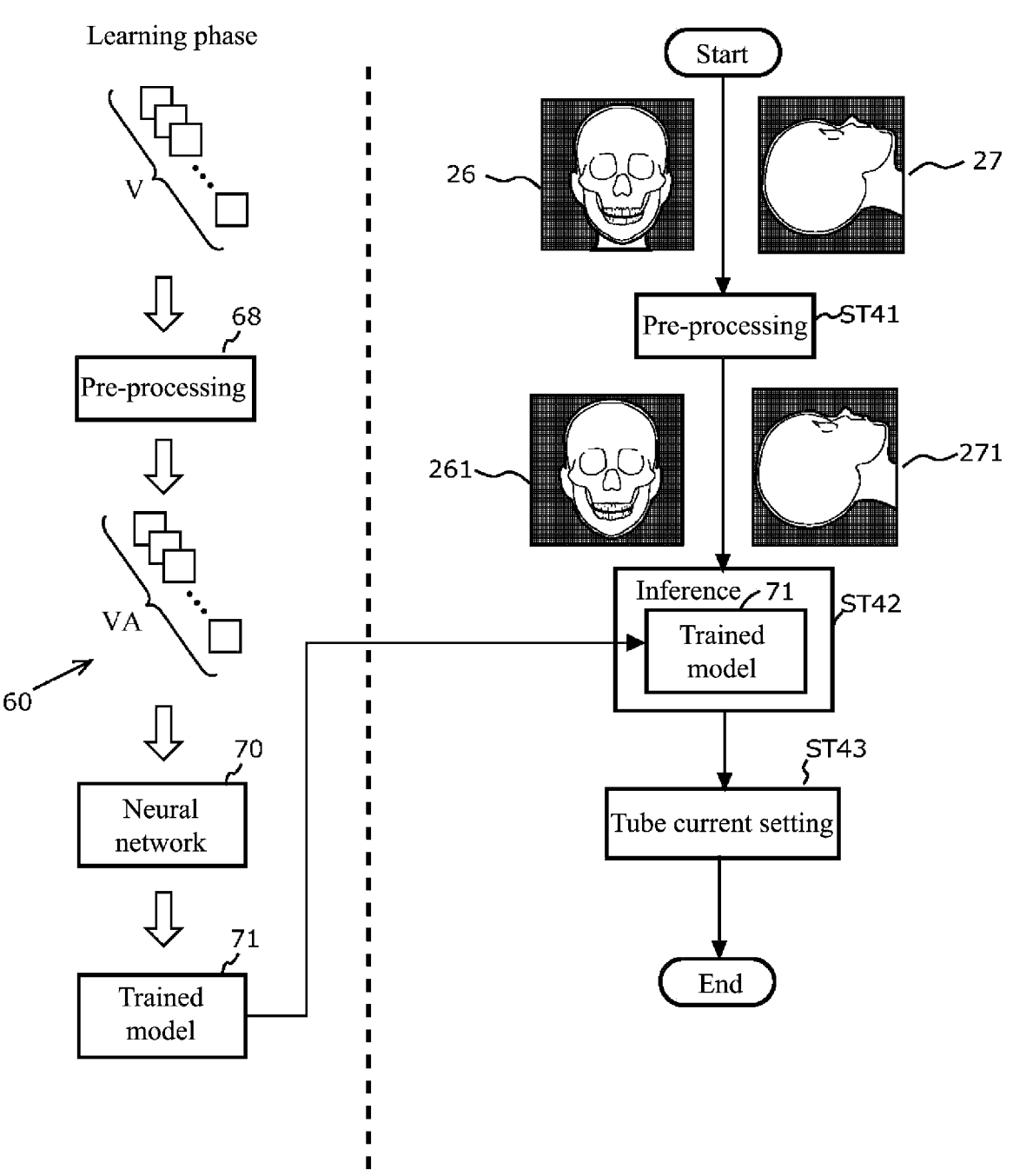
FIG. 23 is a diagram illustrating a flow for identifying an organ having high sensitivity to radiation using a trained model.

FIG. 23 is a diagram illustrating a flow for identifying an organ having high sensitivity to radiation using a trained model. First, we describe how to generate a trained model that is used to identify organs that are highly sensitive to radiation. A trained model is created in advance during the learning phase prior to testing the subject body 112.

In the learning phase, first, an original images set V is prepared. The original images set V includes, for example, a plurality of scout images acquired by executing a scan with the X-ray tube positioned at an angle of 0° and a plurality of scout images acquired by executing a scan with the X-ray tube positioned at an angle of 90°. Note that the original images set V may optionally include scout images obtained by executing a scan with the X-ray tube positioned at an angle other than 0° and 90°. Next, preprocessing 68 is performed on the original images set V, as illustrated in FIG. 23.

The pre-processing 68 includes, for example, image cropping, standardization, normalization, image inversion, image rotation, a magnification percentage change, and an image quality change. By performing preprocessing on the original images set V, a set VA of preprocessed scout images can be obtained. The set VA of preprocessed scout images is used as training data 60 for creating the trained model.

Next, the training data 60 is used to train the neural network 70. The neural network can use, for example, a convolutional neural network. In Embodiment 1, the neural network is trained to create a trained model 71 so as to output position data representing regions of organs (eyes) highly sensitive to radiation. This trained model 71 is stored in the storing device 218 (see FIG. 2). The trained model 71 may be stored on an external storing device accessible by the CT device. Therefore, the trained model 71 can be used to infer the eye position.

The right side of FIG. 23 illustrates the flow of inferring the eye position using the trained model 71. In step ST41, the computer 216 preprocesses scout images 26 and 27 obtained by scout scanning. In step ST42, the computer 216 inputs the preprocessed scout images 261 and 271 as input images to the trained model 71, and uses the trained model 71 to infer the positions of eyes that are highly sensitive to radiation. After inferring eye positions, processing proceeds to step ST43. In step ST43, the computer 216 sets the tube current of the X-ray tube 104 based on the inferred eye position and rotation angle θ so as to selectively reduce eye exposure during the diagnostic scan (see FIG. 24).

Figure 24:
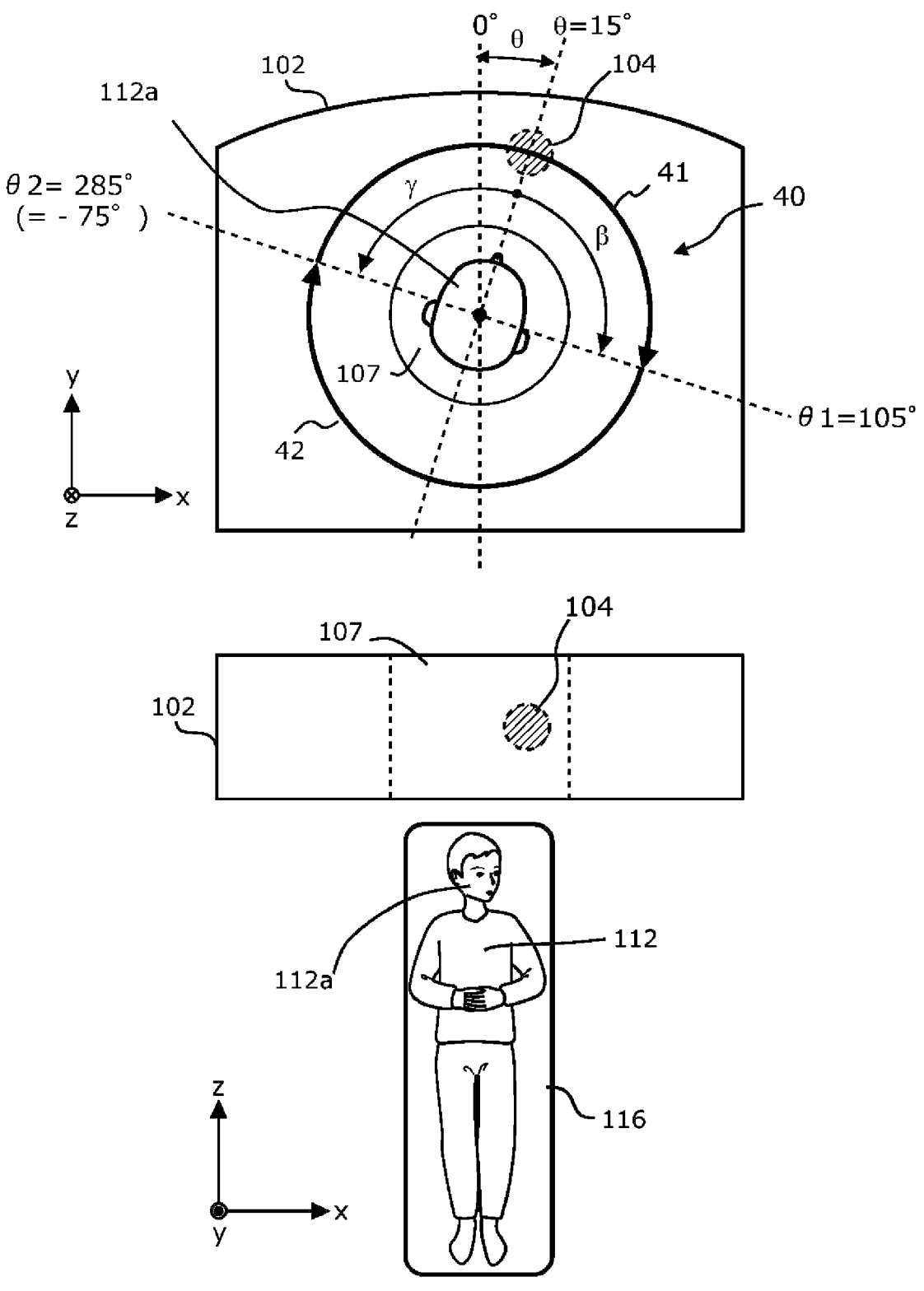
FIG. 24 is an explanatory diagram of a method of determining weighting coefficients.

FIG. 24 is an explanatory diagram of a method of determining weighting coefficients. Based on the rotation angle θ of the head 112a of the subject body 112, the computer 216 first determines an angle θ1 rotated clockwise from the rotation angle θ by an angle β and an angle θ2 rotated counterclockwise from the rotation angle θ by an angle γ. Although β=γ=90° in Embodiment 1, β and γ may be angles other than 90°, and β≠γ is feasible as well. In Embodiment 1, since the rotation angle θ is θ=15°, calculation provides θ1=θ+β=15°+90°=105°, and θ2=θ−γ=15°−90°=−75°. Assuming that the clockwise direction from 0° is the positive direction, −75° becomes +285°, so the following description will be continued with θ2=285°.

Next, based on θ1=105° and θ2=285°, the computer 216 divides the path 40 along which the X-ray tube 104 moves into a path 41 on the side where the eyes of the head 112a are positioned and a path 42 on the side opposite the eyes (occipital side) of the head 112a.

In addition, the computer 216 also identifies the period during which the eyes are irradiated with X-rays during the diagnostic scan. Since the eyes are located on the surface side of the face of the subject body 112, the X-ray tube 104 on path 41 moves closer to the eye than the X-ray tube 104 on path 42. Therefore, the computer 216 sets the tube current of the X-ray tube 104 while moving along the path 41, while X-rays are irradiated to the eyes, to be lower than the tube current of the X-ray tube 104 while moving along the path 42. The tube current is set in this manner. After the preparation for the diagnostic scan is complete, processing proceeds to step ST5 (see FIG. 14).

At step ST5, a diagnostic scan of the head 112a is performed. In a diagnostic scan, the tube current is adjusted such that the tube current of the X-ray tube 104 is low while the X-ray tube 104 is moving on the path 41 when X-rays are irradiated to the eyes. Therefore, the exposure of eyes that are highly sensitive to radiation can be selectively reduced. In Embodiment 1, when determining the path 41, β=γ=90° was used, but β and γ may be angles other than 90°. For example, if further reduction in eye exposure is desired, β and γ can be set to angles greater than 90° (for example, 100°).

Figure 25:
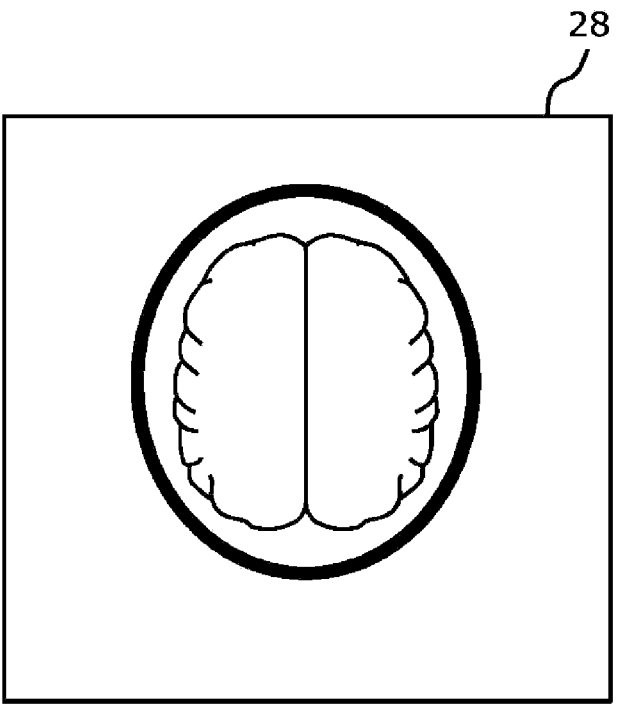
FIG. 25 is a diagram illustrating a reconstructed CT image 28.
Figure 25:
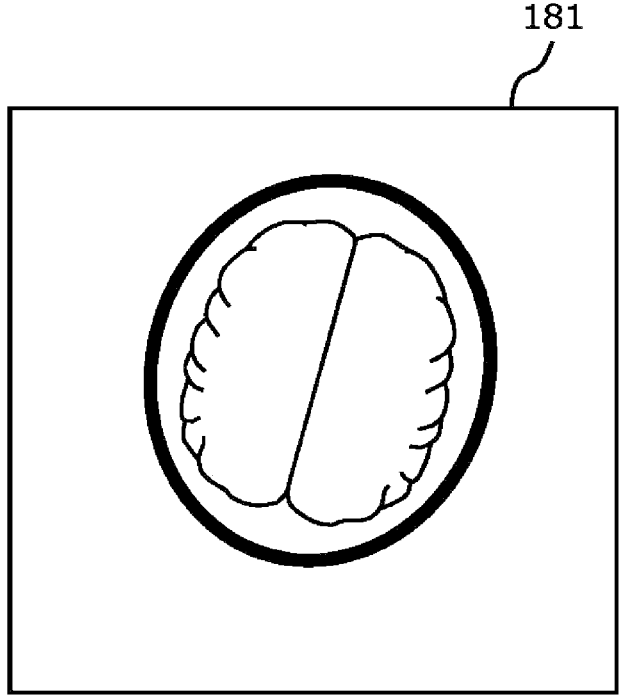

X-rays irradiated from the X-ray tube 104 are detected by the X-ray detector 108. The projection data detected by the X-ray detector 108 is collected by the DAS 214. The DAS 214 performs prescribed processing, including sampling, digital conversion, and the like, on the acquired projection data and transmits the data to the computer 216 or image reconstruction unit 230. On the computer 216 or image reconstruction unit 230, a processor reconstructs the CT image for diagnosis based on the data obtained from the scan. When reconstructing a CT image, the processor considers that the rotation angle θ of the head 112a is θ=15°, and reconstructs the CT image such that the rotation angle θ of the head depicted in the CT image changes from 15° to 0°. Therefore, the processor can reconstruct a CT image corrected so that the rotation angle of the head 112a is 0°. FIG. 25 is a diagram illustrating a reconstructed CT image 28. For comparison, FIG. 25 also illustrates a CT image 181 reconstructed without correcting the rotation angle θ=15° of the head 112a. As illustrated in FIG. 24, the head 112a of the subject body 112 on the table 116 is tilted 15° but the rotation angle of the head 112a is corrected to 0° during image reconstruction so the CT image 28 is displayed with the tilt of the head 112a corrected. Thus, the flow of FIG. 14 ends.

In Embodiment 1, the rotation angle θ of the head 112a of the subject body 112 is determined and the position (angle) of the X-ray tube 104 is set based on this rotation angle θ for executing the scout scan. Therefore, even if the subject body 112 can not face directly upwards (see FIG. 20), scout images 26 and 27 (see FIG. 21) that are substantially the same as the scout images 16 and 17 (see FIG. 8) obtained when the subject body 112 faces directly upwards can be obtained. Therefore, even if the subject body 112 can not face directly upward, the scout image 26 captured from the front of the face of the subject body 112 and the scout image 27 captured from the side of the face of the subject body 112 can be obtained. In Embodiment 1, segmentation is executed based on the scout images 26 and 27, enabling segmentation accuracy of the scout images to be improved.

In addition, the CT image 28 (see FIG. 25) obtained by means of the diagnostic scan has the rotation angle θ of the head 112a corrected from a rotation angle θ of the head 112a of 15° to 0°. Therefore, since the display device 232 (see FIG. 2) displays the CT image 18 for the case of simulating the face of the subject body 112 facing directly upwards, the doctor can focus on interpretation work without being conscious that the face of the subject body 112 is obliquely oriented.

In Embodiment 1, the subject body is imaged from two directions (15° and 105°) to obtain scout images 26 and 27 (see FIG. 21). However, it is also possible to image the subject body from only one of the two directions (15° and 105°) and obtain only one of the scout images 26 and 27.

In Embodiment 1, the X-ray tube 104 is positioned at an angle of 15° (in other words, the X-ray tube 104 is positioned on the surface side of the face of the subject body 112), and X-rays are irradiated from the surface side of the face of the subject body 112 to obtain the scout image 26. However, even if instead of positioning the X-ray tube 104 at an angle of 15°, the X-ray tube 104 is positioned at an angle of 195° that is the opposite side of 15° (in other words, positioning the X-ray tube 104 on the back of the head side of the subject body 112), and X-rays are irradiated from the back of the head side of the subject body 112, a scout image including substantially the same morphological information and/or functional information as the scout image 26 can be obtained. Therefore, the scout image may be obtained by positioning the X-ray tube 104 at an angle of 195° instead of 15° and irradiating the subject body 112 with X-rays from the back side of the head.

In addition, in Embodiment 1, the X-ray tube 104 is positioned at an angle of 105° (in other words, the X-ray tube 104 is positioned on the left side of the subject body 112), and X-rays are irradiated from the left side of the subject body 112 to obtain the scout image 27. However, even if instead of positioning the X-ray tube 104 at an angle of 105°, the X-ray tube 104 is positioned at an angle of 285° that is the opposite side of 105° (in other words, positioning the X-ray tube 104 on the right side of the subject body 112), and X-rays are irradiated from the right side of the subject body 112, a scout image including substantially the same morphological information and/or functional information as the scout image 27 can be obtained. Therefore, the scout image may be obtained by positioning the X-ray tube 104 at an angle of 285° instead of 105° and irradiating the subject body 112 with X-rays from the right side.

Further, in Embodiment 1, in step ST22, the head of the subject body 112 is approximated as an object 22 (for example, a sphere, an ellipsoid) having a symmetrical shape with respect to the YZ plane, and the reference plane 32 is determined based on this object 22. However, instead of determining the reference plane 32 based on the object 22, a plane parallel to the YZ plane may be registered in advance as the reference plane 32 in the storing device. By registering a plane parallel to the YZ plane as the reference plane 32 in the storing device, the rotation angle θ can be determined without executing step ST22, thereby simplifying the flow of step ST20.

Figure 26:
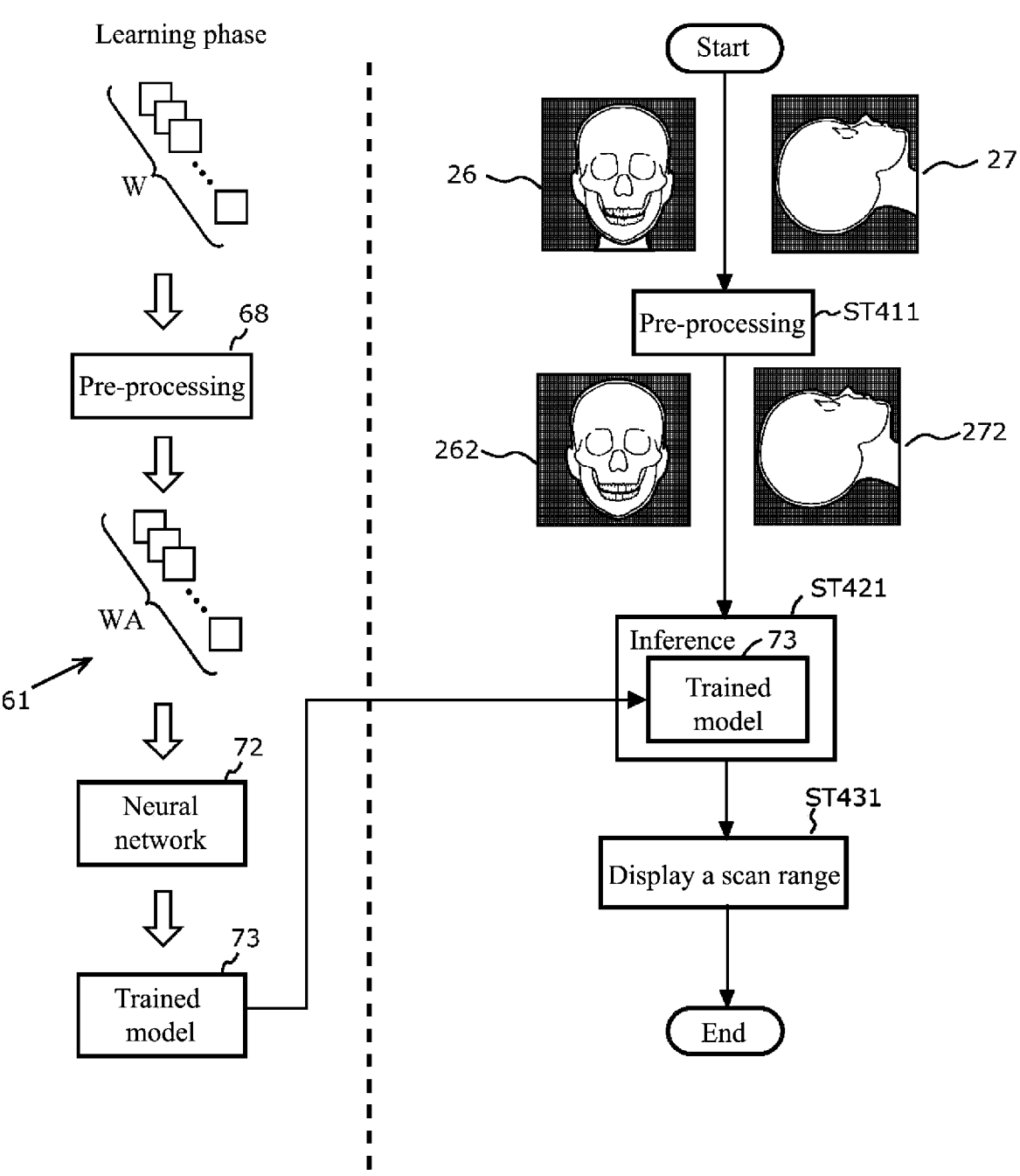
FIG. 26 is a diagram illustrating a flow of automatically setting a scan range using a trained model.

In Embodiment 1, the operator manually sets the scan range of the diagnostic scan in step ST4 (see FIG. 14) but in Embodiment 2, a method of automatically setting the scan range using a trained model will be described. FIG. 26 is a diagram illustrating a flow of automatically setting a scan range using a trained model. First, a method of generating a trained model used to set the scan range will be described. A trained model is created in advance during the learning phase prior to testing the subject body 112.

In the learning phase, first, an original images set W is prepared. The original images set W includes, for example, a plurality of scout images acquired by executing a scan with the X-ray tube 104 positioned at an angle of 0° and a plurality of scout images obtained by executing a scan with the X-ray tube 104 positioned at an angle of 90°. Note that if needed, the original images set W may include scout images obtained by performing scans with the X-ray tube 104 positioned at angles other than 0° and 90°. Next, preprocessing 68 is executed on the original images set W, as illustrated in FIG. 26.

The pre-processing 68 includes, for example, image cropping, standardization, normalization, image inversion, image rotation, a magnification percentage change, and an image quality change. By preprocessing the original images set W, a set WA of preprocessed scout images can be obtained. The set WA of preprocessed scout images is used as training data 61 for creating the trained model.

Next, the training data 61 is used to train the neural network 72. For the neural network 72, a convolutional neural network can be used, for example. In the Embodiment 2, the neural network 72 is trained to create a trained model 73 so as to output scan range data indicating the start position and end position of the scan range. This trained model 73 can be stored in the storing device 218.

Figure 27:
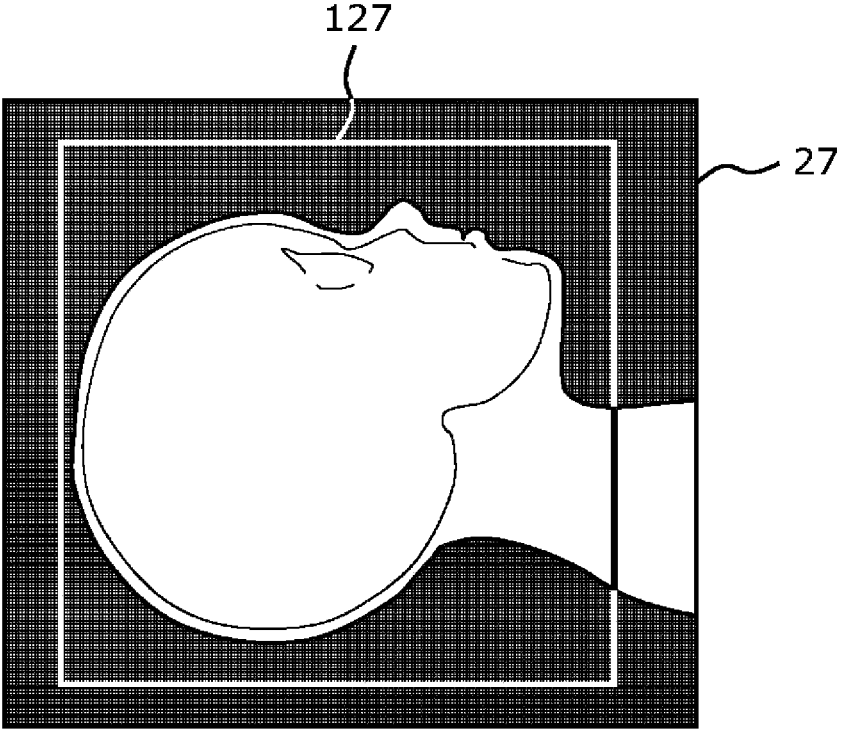
FIG. 27 is a schematic view of a scout image 27 and an inferred scan range 127 displayed on a display device.

Therefore, the computer 216 can use the trained model 73 to infer the start and end positions of the scan range. The right side of FIG. 26 shows the flow of inferring the scan range using the trained model 73. In step ST411, the computer 216 preprocesses scout images 26 and 27 obtained by scout scanning. In step ST421, the computer 216 inputs the preprocessed scout images 262 and 272 as input images to the trained model 73, and uses the trained model 73 to infer the scan start position and scan end position of the scan range. At step ST431, the computer 216 displays the inferred scan range on the scout image 27. FIG. 27 is a schematic view of a scout image 27 and an inferred scan range 127 displayed on a display device. The flow is completed in this manner.

In Embodiment 2, a scan range 127 is inferred based on the scout image 26 obtained by positioning the X-ray tube 104 at an angle of 15° (position P15) and the scout image 27 obtained by positioning the X-ray tube 104 at an angle of 105° (position P105). Therefore, even if the subject 112 cannot face directly upwards in the supine position and is obliquely oriented, the scan range can be inferred based on the scout image 26 taken from the front of the face of the subject body 112 and the scout image 27 taken directly to the side of the face of the subject body 112, thus improving the accuracy of inferring the scan range.

Figure 28:
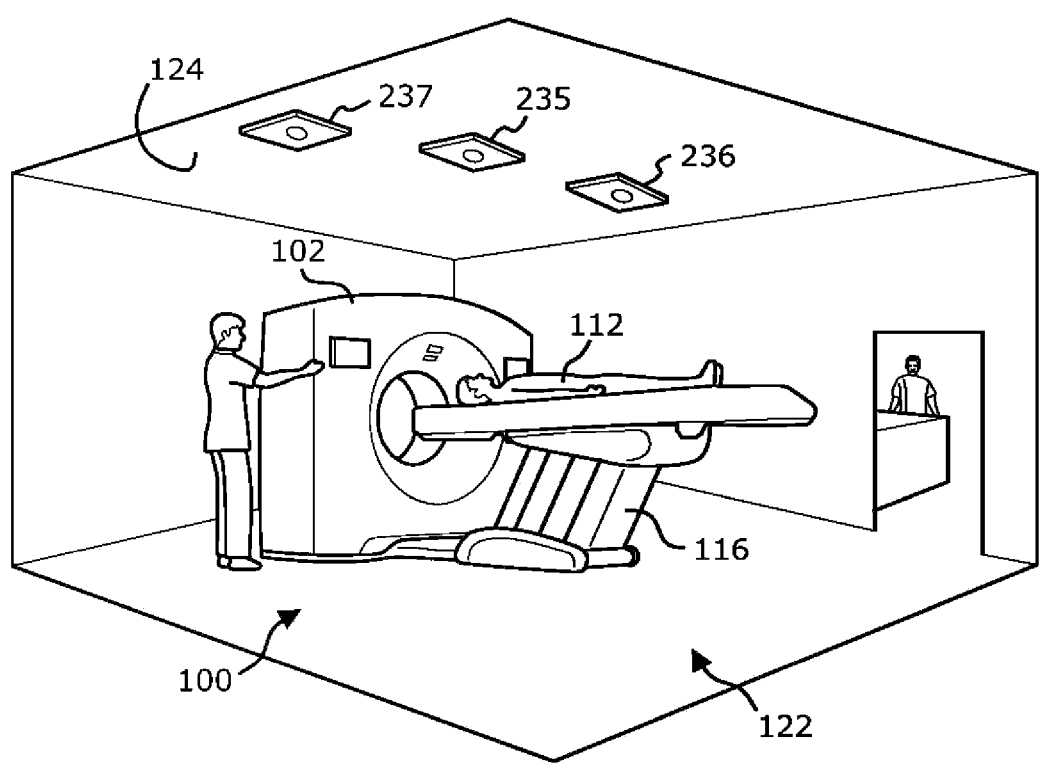
FIG. 28 is a diagram illustrating a plurality of cameras provided in a scan room in Embodiment 3.

In Embodiment 3, a plurality of cameras are provided, and an example of selecting a camera image suitable for obtaining the rotation angle θ of the head 112$a$ from the camera images photographed by the plurality of cameras will be described. FIG. 28 is a diagram illustrating a plurality of cameras provided in a scan room in Embodiment 3.

The scan room 122 is equipped with a plurality of cameras. In Embodiment 3, an example in which three cameras 235, 236, and 237 are provided on the ceiling 124 of the scan room 122 will be described, but two cameras may be provided, or four or more cameras may be provided.

Figure 29:
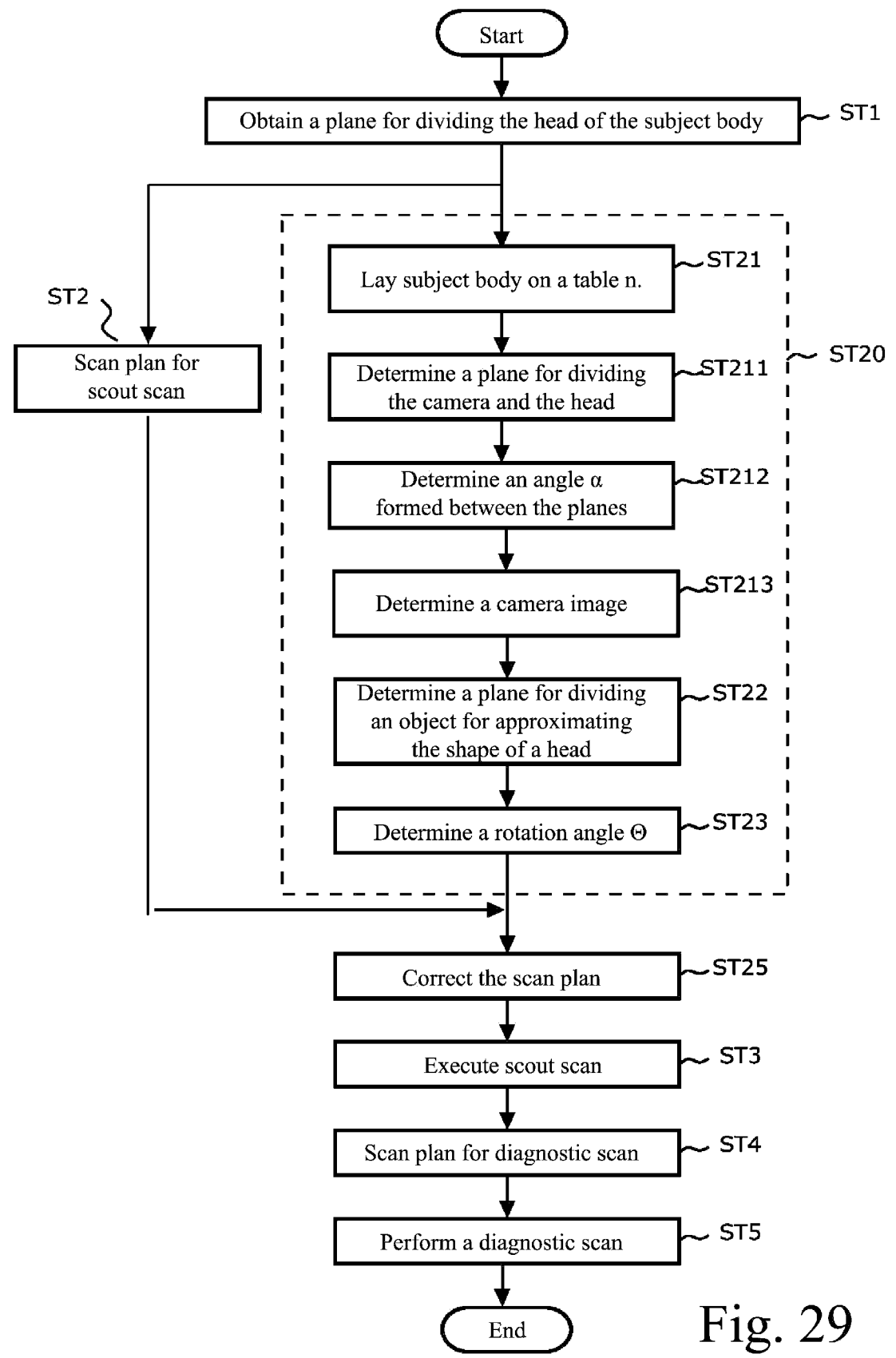
FIG. 29 is a diagram illustrating the flow in Embodiment 3.
Figure 30:
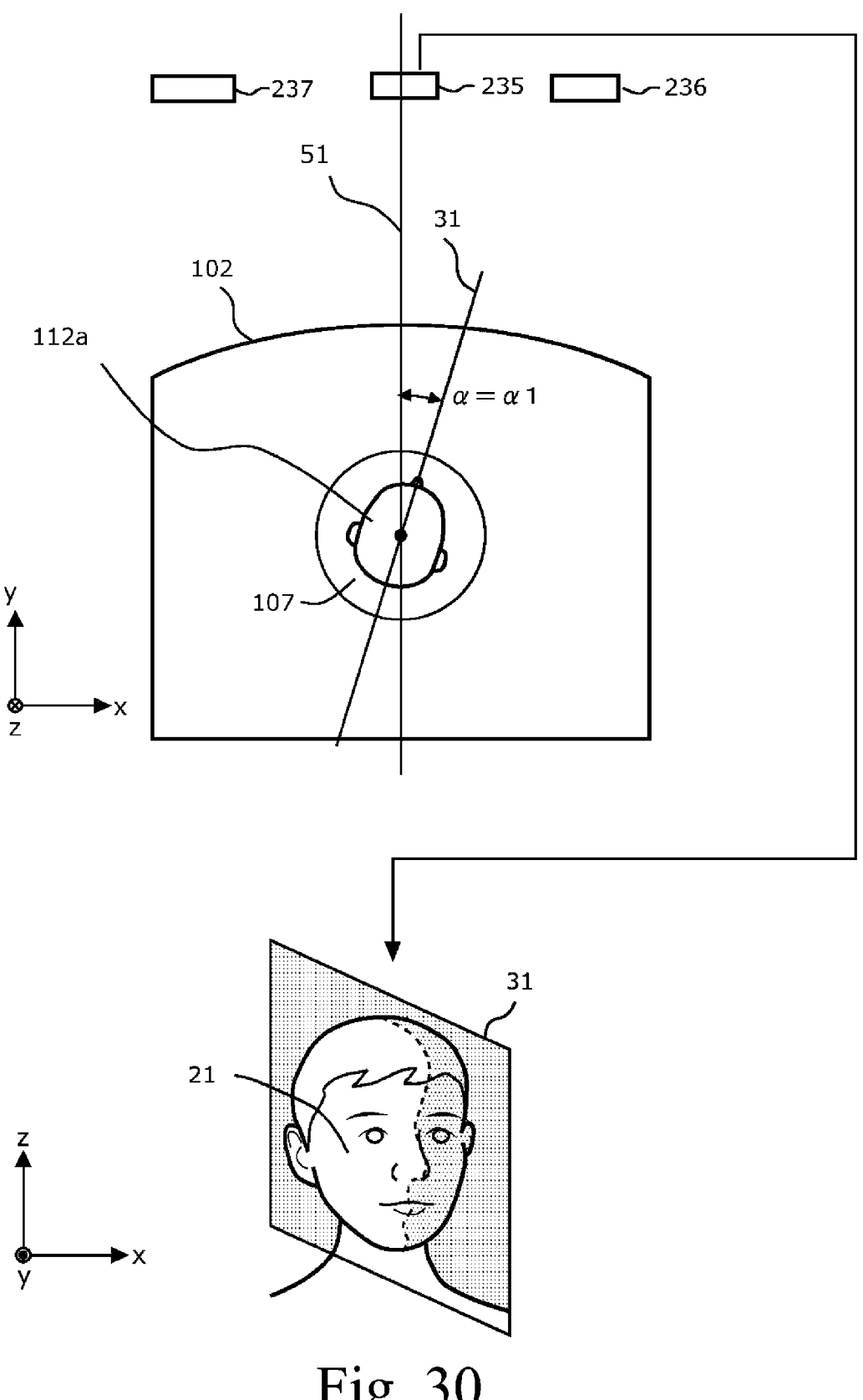
FIG. 30 is an explanatory diagram of step ST20 in Embodiment 3.

FIG. 29 is a diagram illustrating the flow in Embodiment 3. In comparison with Embodiment 1, Embodiment 3 is different in step ST20, but other steps are the same as those in Embodiment 1. Therefore, in describing Embodiment 3, step ST20 will be mainly described. FIG. 30 is an explanatory diagram of step ST20 in Embodiment 3.

In step ST21, the computer 216 (see FIG. 2) extracts a plurality of feature points (for example, eyebrows, eyes, nose, mouth, and jaw) on the face surface of the subject body 112 from the camera image 21 of the subject 112 acquired by the camera 235. Furthermore, as illustrated in FIG. 30, the computer 216 obtains a central plane 31 that divides the head 112$a$ of the subject body 112 into left and right based on the plurality of extracted feature points. After determining the central plane 31, processing proceeds to step ST211.

In step ST211, the computer 216 determines a plane 51 that traverses the camera 235 and head 112$a$ and is parallel to the Z-axis direction (axial direction) based on position data indicating the position of the camera 235 and position data indicating the position of the head 112$a$ of the subject body 112. Note that the position data indicating the position of the camera 235 is data obtained in advance before the examination of the subject body 112, and is stored in a storing device (for example, the storing device 218). The computer 216 can retrieve position data indicating the position of the camera 235 from a storing device. Position data indicating the position of the head 112$a$ of the subject body 112 is data that can be obtained based on the camera image 21. Therefore, the computer 216 can determine the plane 51 that traverses the camera 235 and the head 112$a$ and is parallel to the Z-axis direction (axial direction). After determining the plane 51, processing proceeds to step ST212.

In step ST212, the computer 216 determines the angle α formed by the plane 31 and plane 51, and obtains this angle α as the angle α indicating the mounting position of the camera 235 with respect to the central plane 31 of the face of the subject body 112. In FIG. 30, it is assumed that α=α1. This α=α1 is stored in a storing device (for example, storing device 218). After determining the angle α=α1 of the camera 235, the angles α of the other cameras 236 and 237 are also obtained according to steps ST21, ST211, and ST212.

Figure 31:
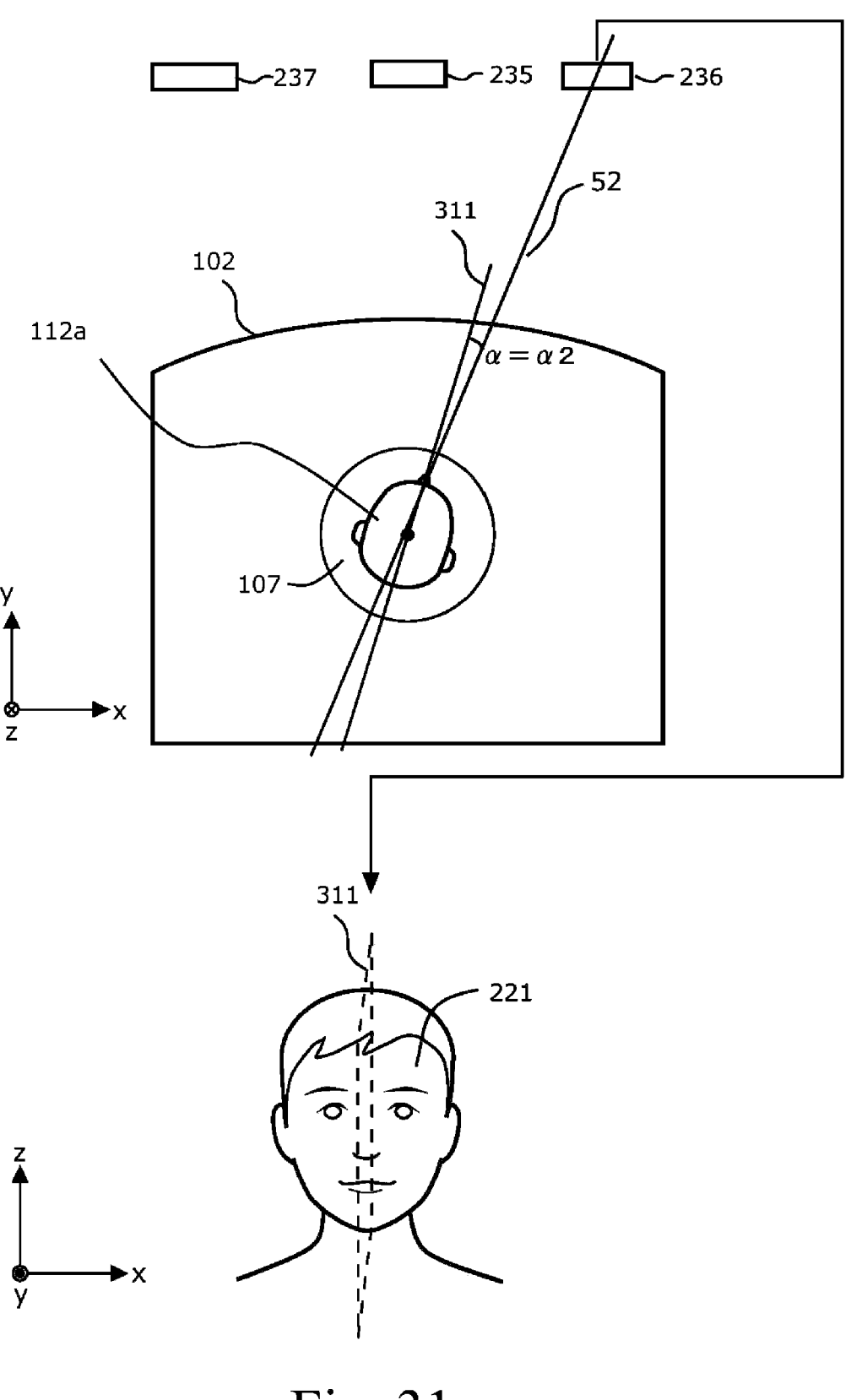
FIG. 31 is an explanatory diagram of a method of obtaining the angle α of a camera 236.

FIG. 31 is an explanatory diagram of a method of obtaining the angle α of the camera 236. In step ST21, the computer 216 extracts a plurality of feature points (for example, eyebrows, eyes, nose, mouth, and jaw) on the face surface of the subject body 112 from the camera image 221 of the subject 112 acquired by the camera 236. Furthermore, as illustrated in FIG. 31, the computer 216 obtains a central plane 311 that divides the head 112$a$ of the subject body 112 into left and right based on the plurality of extracted feature points.

In step ST211, the computer 216 determines a plane 52 that traverses the camera 236 and head 112$a$ and is parallel to the Z-axis direction (axial direction) based on position data indicating the position of the camera 236 and position data indicating the position of the head 112$a$ of the subject body 112. Note that the position data indicating the position of the camera 236 is data obtained in advance before the examination of the subject body 112, and is stored in a storing device (for example, the storing device 218). The computer 216 can retrieve position data indicating the position of the camera 236 from a storing device. Position data indicating the position of the head 112$a$ of the subject body 112 is data that can be obtained based on the camera image 221. Therefore, the computer 216 can determine the plane 52 that traverses the camera 236 and the head 112*a* and is parallel to the Z-axis direction (axial direction). After determining the plane 52, processing proceeds to step ST212.

In step ST212, the computer 216 determines the angle α formed by the plane 311 and plane 52, and obtains this angle α as the angle α indicating the mounting position of the camera 236 with respect to the central plane 311 of the face of the subject body 112. In FIG. 31, it is assumed that α=α2. This α=α2 is stored in the storing device. After determining the angle α=α2 of the camera 236, the angles α of the other camera 237 are also obtained according to steps ST21, ST211 and ST212.

Figure 32:
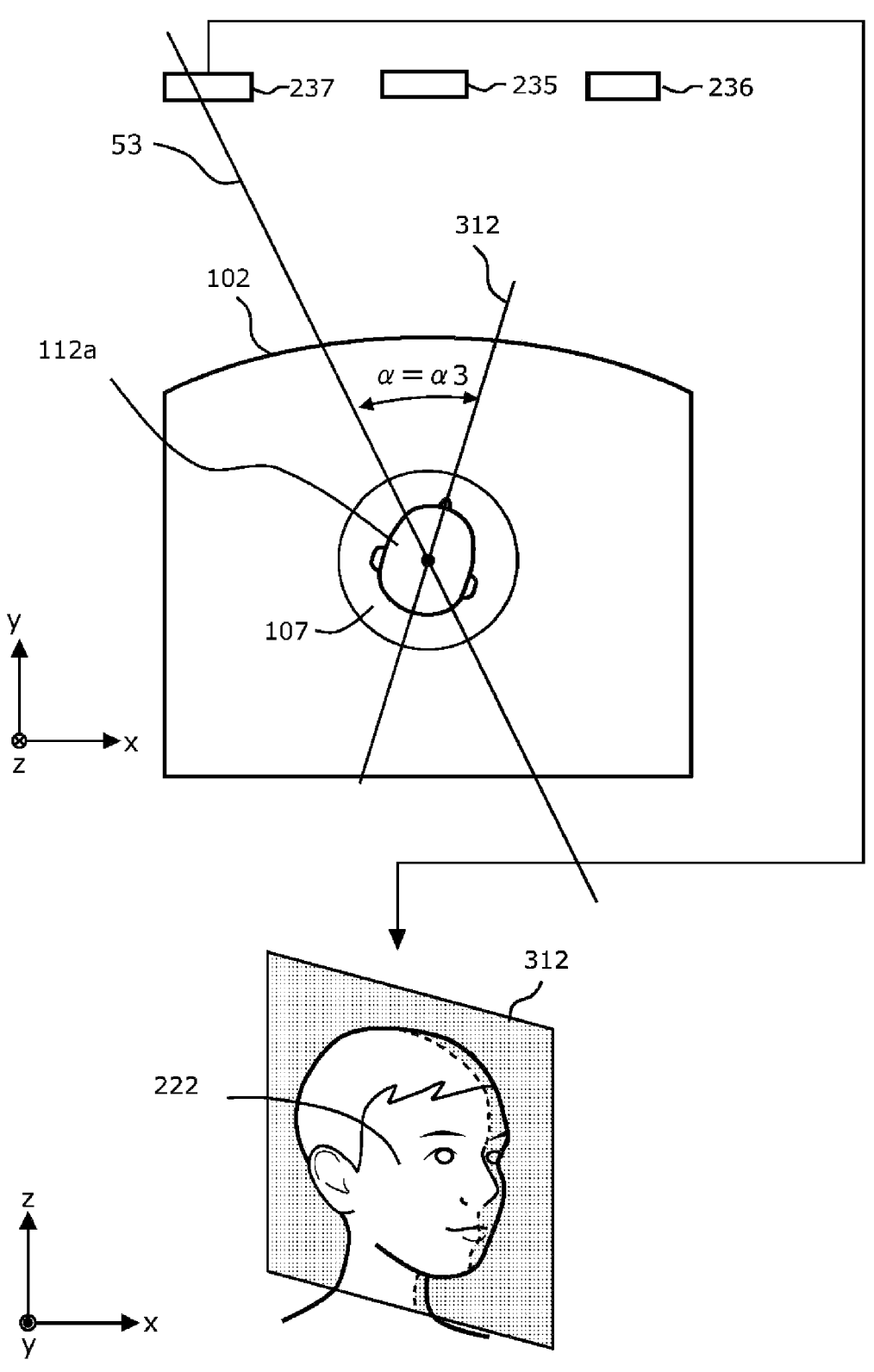
FIG. 32 is an explanatory diagram of a method of obtaining the angle α of a camera 237.

FIG. 32 is an explanatory diagram of a method of obtaining the angle α of a camera 237. In step ST21, the computer 216 extracts a plurality of feature points (for example, eyebrows, eyes, nose, mouth, and jaw) on the face surface of the subject body 112 from the camera image 222 of the subject 112 acquired by the camera 237. Furthermore, as illustrated in FIG. 32, the computer 216 obtains a central plane 312 that divides the head 112*a* of the subject body 112 into left and right based on the plurality of extracted feature points.

In step ST211, the computer 216 determines a plane 53 that traverses the camera 237 and head 112*a* and is parallel to the Z-axis direction (axial direction) based on position data indicating the position of the camera 237 and position data indicating the position of the head 112*a* of the subject body 112. Note that the position data indicating the position of the camera 237 is data obtained in advance before the examination of the subject body 112, and is stored in a storing device. The computer 216 can retrieve position data indicating the position of the camera 237 from a storing device. Position data indicating the position of the head 112*a* of the subject body 112 is data that can be obtained based on the camera image 222. Therefore, the computer 216 can determine the plane 53 that traverses the camera 237 and the head 112*a* and is parallel to the Z-axis direction (axial direction). After determining the plane 53, processing proceeds to step ST212.

In step ST212, the computer 216 determines the angle α formed by plane 312 and plane 53, and obtains this angle α as the angle α indicating the mounting position of the camera 237 with respect to the central plane 312 of the face of the subject body 112. In FIG. 32, it is assumed that α=α3. This α=α3 is stored in the storing device.

Therefore, the angles α of cameras 235, 236, and 237 can be calculated as α1, α2, and α3, respectively. After calculating these angles α1, α2, and α3, processing proceeds to step ST213. In step ST213, the computer 216 determines the rotation angle θ of the head 112*a* of the subject body 112 from the camera image 21 (see FIG. 30), the camera image 221 (see FIG. 31), and the camera image 222 (see FIG. 32) and determines which camera image to use. The rotation angle θ of the head 112*a* of the subject body 112 is a value determined with reference to the central plane that divides the face of the subject body 112 into left and right. Therefore, in order to determine the rotation angle θ of the head 112*a* of the subject body 112 as accurately as possible, determining the central plane dividing the face of the subject body 112 into left and right as accurately as possible is important. Since the central plane is determined using the camera image, determining the central plane based on the camera image obtained from the camera positioned directly in front of the face of the subject body 112 is considered ideal for determining the central plane as accurately as possible. Therefore, in Embodiment 3, of the camera images 21, 221, and 222 (see FIG. 30 to FIG. 32), the camera image acquired from the camera closest to the position directly in front of the face of the subject body 112 is set as the camera image used to determine the rotation angle θ of the head. Of the cameras 235, 236, and 237, the camera closest to the position directly in front of the subject body 112 is the camera with the smallest angle α. The closer the camera is to the position directly in front of the face of the subject body 112, the smaller the value of the angle α of the camera. Therefore, by specifying the smallest angle from among the angles α1, α2, and α3, the camera closest to the position directly in front of the face of the subject body 112 can be specified. In Embodiment 3, among the camera angles α1, α2, and α3, the minimum value is α2. Therefore, of cameras 235, 236, and 237, the computer 216 specifies the camera 236 with angle α2 as the camera closest to the position directly in front of the face of the subject body 112. Furthermore, the computer 216 determines the camera image 221 (see FIG. 31) acquired by the camera 236 as the camera image to be used for determining the rotation angle θ of the head 112*a* of the subject body 112. After determining the camera image 221, processing proceeds to step ST22.

In step ST22, as described in Embodiment 1, the reference plane 32 (see FIG. 16) for dividing the object 22 approximating the shape of the head 112*a* is obtained. In step ST23, the angle between the central plane 311 (see FIG. 31) determined from camera image 221 and the reference plane 32 is obtained as the rotation angle θ of the head.

Since step ST25 and subsequent steps are the same as those in Embodiment 1 or Embodiment 2, the description thereof will be omitted. In Embodiment 3, of the camera images 21, 221, and 222 (see FIG. 30 to FIG. 32), the camera image 221 acquired from the camera closest to the position directly in front of the face of the subject body 112 is set as the camera image used to determine the rotation angle θ of the head. Therefore, the rotation angle θ of the head can be calculated using the highly reliable central plane 311 as a plane dividing the face of the subject body into right and left. Therefore, accuracy of scout image segmentation can be improved and the quality of CT images obtained by diagnostic scanning can be further improved.

In Embodiments 1 to 3, the case of imaging the head 112*a* of the subject body 112 has been described. However, the present invention is not limited to imaging the head 112*a*, and can be applied to imaging portions other than the head 112*a*. For example, when imaging the chest, the orientation of the chest can be obtained based on the difference in height between the left and right shoulders. Also, when the imaging region is the abdomen, the orientation of the abdomen can be determined based on the difference in height on the left and right sides of the waist. Furthermore, if the imaging region includes the chest and abdomen, the orientation of the imaging region can be determined based on both the difference in height between the left and right shoulders and the difference in height between the left and right sides of the waist.

Incidentally, in Embodiments 1 to 3, an example using a CT device as a medical device is indicated. However, the medical device of the present invention is not limited to a CT device, and application to medical devices that irradiate a subject body with an X-ray source (for example, a PET-CT device) is feasible.

The invention claimed is:

1. A medical device, comprising:
a gantry including an X-ray tube that is rotatable on a path centered on a rotation axis and an X-ray controller that controls the X-ray tube;
a table to support a subject; and
at least one processor;
the medical device executing a first scan on the subject, wherein
the at least one processor executes operations including:
determining a first position on the path for arranging the X-ray tube for the first scan based on a direction a portion of the subject to be imaged is facing, wherein the direction of the portion of the subject is determined using images from a camera, and
controlling the X-ray tube by means of the X-ray controller such that the X-ray tube irradiates X-rays from said first position.

2. The medical device according to claim 1, wherein the portion to be imaged includes a head and determining the direction the portion to be imaged is facing includes determining a first plane where a face of the subject is divided into left and right based on the image and determining a rotation angle of a subject head based on said first plane.

3. The medical device according to claim 2, wherein determining the rotation angle of the subject head includes determining an angle between the first plane and a second plane of the face of the subject divided into left and right for a case that the face of the subject is facing an ideal direction.

4. The medical device according to claim 3, wherein determining the direction the portion to be imaged is facing includes approximating a subject face as an object having a shape that is symmetrical with respect to a plane that is parallel to a body axis direction and vertical direction and determining a dividing plane that divides in a direction perpendicular to the body axis direction and to the vertical direction as the second plane.

5. The medical device according to claim 3, further comprising:
a gantry motor controller to control the gantry motor for rotating the X-ray tube, wherein the at least one processor executes operations including:
controlling the gantry motor by means of the gantry motor controller to move the X-ray tube from the first position to a second position by rotating over a prescribed angle, and
controlling the X-ray tube by means of the X-ray controller causing the X-ray tube to irradiate X-rays from the second position.

6. The medical device according to claim 5, wherein a first scan plan for executing the first scan is set to an angle corresponding to a first initial position of the X-ray tube when the first scan is executed and the at least one processor executes operations including correcting the angle corresponding to the first initial position to the angle corresponding to the first position.

7. The medical device according to claim 6, wherein a second scan plan for executing the first scan is set to an angle corresponding to a second initial position of the X-ray tube when the first scan is executed and the at least one processor executes operations including correcting the angle corresponding to the second initial position to the angle corresponding to the second position.

8. The medical device according to claim 7, wherein the at least one processor executes operations including reconstructing a first scout image based on data acquired according to a post-corrected first scan plan.

9. The medical device according to claim 8, wherein the at least one processor executes operations including reconstructing a second scout image based on data acquired according to a post-corrected second scan plan.

10. The medical device according to claim 9, wherein the at least one processor identifies an organ that has high sensitivity to radiation based on the first scout image and the second scout image.

11. The medical device according to claim 10, wherein the at least one processor executes operations including generating an input image by preprocessing the first scout image and the second scout image, inputting the input image to a trained model, and estimating the position of organs with high sensitivity to irradiation.

12. The medical device according to claim 10, wherein the at least one processor sets a tube current of the X-ray tube so as to selectively reduce exposure of the organ in the second scan executed after the first scan based on an identified organ position and rotation angle.

13. The medical device according to claim 9, wherein the at least one processor sets a scan range based on the first scout image and the second scout image.

14. The medical device according to claim 13, wherein the at least one processor executes operations including generating an input image by means of preprocessing the first scout image and the second scout image, inputting the input image to a trained model, and estimating a scan start position and a scan end position for the scan range of the second scan that is executed after the first scan.

15. The medical device according to claim 3, wherein the at least one processor decides the image for determining the rotation angle from among a plurality of images acquired from different cameras.

16. The medical device according to claim 3, wherein the at least one processor executes operations including reconstructing a medical image of the portion of the subject to be imaged based on data acquired in a second scan executed after the first scan and reconstructs the medical image such that in reconstructing the medical image, the rotation angle of the head depicted in the medical image is 0°.

17. A method of scanning, comprising:
executing a first scan on a subject using a medical device including: a gantry having an X-ray tube that is rotatable on a path centered on a rotation axis and an X-ray controller that controls the X-ray tube, and a table to support the subject;
determining a first position on the path for positioning the X-ray tube for the first scan based on a direction that a portion of the subject to be imaged is facing, wherein the direction of the portion of the subject is determined using images from a camera; and
controlling the X-ray tube by means of the X-ray controller such that the X-ray tube irradiates X-rays from said first position.

18. A storage medium readable by a computer in a non-transitory manner storing one or more instructions executable by one or more processors, wherein
the storage medium is contained in a medical device that includes a gantry having an X-ray tube that is rotatable on a path centered on a rotation axis and an X-ray controller that controls the X-ray tube and a table to support a subject, and
the one or more instructions determines, upon execution by the one or more processors, a first position on the path for positioning the X-ray tube for a first scan based on a direction a portion of the subject faces and controls the X-ray tube by means of the X-ray controller such that the X-ray tube irradiates X-rays from said first position, wherein the direction of the portion of the subject is determined using images from a camera.

\* \* \* \* \*